US011883456B2

(12) United States Patent
Lundin et al.

(10) Patent No.: US 11,883,456 B2
(45) Date of Patent: *Jan. 30, 2024

(54) FORMULATIONS FOR WEIGHT LOSS AND METHODS OF USE

(71) Applicant: GOLO LLC, Newark, DE (US)

(72) Inventors: Christopher Brian Lundin, Newark, DE (US); Terry Shirvani, Newark, DE (US)

(73) Assignee: GOLO, LLC, Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/812,068

(22) Filed: Jul. 12, 2022

(65) Prior Publication Data

US 2022/0347252 A1 Nov. 3, 2022

Related U.S. Application Data

(63) Continuation of application No. 17/139,141, filed on Dec. 31, 2020, now Pat. No. 11,458,182, which is a continuation of application No. 16/868,918, filed on May 7, 2020, now Pat. No. 11,141,448, which is a continuation of application No. 15/887,666, filed on Feb. 2, 2018, now Pat. No. 10,765,718.

(60) Provisional application No. 62/453,890, filed on Feb. 2, 2017.

(51) Int. Cl.
| | | |
|---|---|---|
| *A61K 36/73* | (2006.01) |
| *A61K 36/41* | (2006.01) |
| *A23L 33/00* | (2016.01) |
| *A61K 33/06* | (2006.01) |
| *A61P 3/00* | (2006.01) |
| *A61K 33/30* | (2006.01) |
| *A61K 36/37* | (2006.01) |
| *A61K 36/185* | (2006.01) |
| *A61K 36/744* | (2006.01) |

(52) U.S. Cl.
CPC .............. *A61K 36/73* (2013.01); *A23L 33/30* (2016.08); *A61K 33/06* (2013.01); *A61K 33/30* (2013.01); *A61K 36/185* (2013.01); *A61K 36/37* (2013.01); *A61K 36/41* (2013.01); *A61K 36/744* (2013.01); *A61P 3/00* (2018.01)

(58) Field of Classification Search
CPC .. A61K 2300/00; A61K 36/185; A61K 36/37; A61K 36/41; A61K 36/73; A61K 36/744; A61K 33/06; A61K 33/30; A23L 33/30; A23L 33/22; A23L 33/40; A23L 33/185; A61P 3/00; A23V 2002/00
USPC ...................................................... 424/641
See application file for complete search history.

(56) References Cited

U.S. PATENT DOCUMENTS

| | | |
|---|---|---|
| 5,215,750 A | 6/1993 | Keane, II |
| 5,480,865 A | 1/1996 | Kingham |
| 5,639,471 A | 6/1997 | Chait et al. |
| 6,039,989 A | 3/2000 | Bangs et al. |
| 6,426,099 B1 | 7/2002 | Terry et al. |
| 7,030,092 B1 | 4/2006 | Levine |
| 7,476,406 B1 | 1/2009 | Smidt |
| 8,349,373 B1 | 1/2013 | Smith |
| 8,420,131 B2 * | 4/2013 | Smith .................... A61K 31/05 424/725 |
| 10,765,718 B2 | 9/2020 | Lundin et al. |
| 2003/0170346 A1 | 9/2003 | McCabe |
| 2003/0226695 A1 | 12/2003 | Mault |
| 2005/0240434 A1 | 10/2005 | Wooten et al. |
| 2005/0249827 A1 * | 11/2005 | Gardiner .................... A61P 3/04 424/773 |
| 2005/0266137 A1 | 12/2005 | Eppler et al. |
| 2006/0040003 A1 | 2/2006 | Needleman et al. |
| 2006/0122468 A1 | 6/2006 | Tavor |
| 2006/0280815 A1 | 12/2006 | Gardiner et al. |
| 2008/0081781 A1 | 4/2008 | Lippa et al. |
| 2008/0124752 A1 | 5/2008 | Ryals et al. |
| 2010/0113494 A1 | 5/2010 | Hu et al. |
| 2011/0151414 A1 | 6/2011 | McCarthy et al. |
| 2011/0189161 A1 | 8/2011 | Blum et al. |
| 2012/0114719 A1 | 5/2012 | Morariu |
| 2014/0234807 A1 | 8/2014 | Lundin |
| 2015/0083635 A1 | 3/2015 | Jacobs et al. |
| 2015/0296835 A1 | 10/2015 | Anderson et al. |

(Continued)

FOREIGN PATENT DOCUMENTS

| | | |
|---|---|---|
| CA | 2361323 C | 8/2014 |
| EP | 0768043 B1 | 11/2003 |

(Continued)

OTHER PUBLICATIONS

International Search Report dated Sep. 3, 2012 in International (PCT) Application No. PCT/ZA2011/000054.
Schaefer, How the Thermic Effect of Foods Can Work to Your Advantage, Examiner.com (May 3, 2010), Web. Sep. 1, 2015. <http://www.examiner.com/article/how-the-thermic-effect-of-foods-can-work-to-your-advantage>.
Anonymous: Specific Dynamic Action—Wikipedia, the free encyclopedia, Feb. 2, 2003, pp. 1-3.

(Continued)

*Primary Examiner* — Audrea B Coniglio
(74) *Attorney, Agent, or Firm* — Barnes & Thornburg LLP; Kenneth E. Horton; Joan Taft Kluger

(57) ABSTRACT

A weight loss composition including banaba leaf extract, apple fruit extract, *Rhodiola* root extract, zinc chelate, and magnesium chelate are described. The weight loss composition may further include *gardenia* fruit extract, chromium chelate, *Salacia* extract, berberine, inositol, or mixtures thereof. Embodiments are also directed to a bulk food product and a weight management plan, which may be used in conjunction with the weight loss composition. Embodiments are also directed to kits and methods of use for treating or preventing obesity, promoting weight loss, and improving insulin resistance.

13 Claims, 3 Drawing Sheets

(56) References Cited

U.S. PATENT DOCUMENTS

| | | |
|---|---|---|
| 2016/0029680 A1 | 2/2016 | Lundin |
| 2016/0196766 A1 | 7/2016 | Lundin |
| 2017/0157193 A1* | 6/2017 | Ling .................. A61K 9/0019 |
| 2018/0214502 A1 | 8/2018 | Lundin et al. |
| 2019/0159505 A1 | 5/2019 | Lundin |
| 2020/0261530 A1 | 8/2020 | Lundin et al. |

FOREIGN PATENT DOCUMENTS

| | | |
|---|---|---|
| JP | 2010202634 A | 9/2010 |
| JP | 2017525389 A | 9/2017 |
| WO | 2002096223 A1 | 12/2002 |
| WO | 2005029242 A2 | 3/2005 |
| WO | 2010104595 A1 | 9/2010 |
| WO | 2015017625 A1 | 2/2015 |

OTHER PUBLICATIONS

International Search Report in International Application No. PCT/IB2014/00137 dated Jun. 25, 2014.

Halton et al., "The Effects of High Protein Diets on Thermogenesis, Satiety and Weight Loss: A Critical Review," J. Amer. Coll. Nutri. (2004), 23(5):373-385.

Barron, Jon. "Exercise Types for Natural Weight Loss." Published Feb. 26, 2007 by Baseline of Health Foundation. <https://jonbarron.org/athletic-performance/need-exercise>.

Frazier, Karen. "Examples of Interval Training." Published Jan. 31, 2010 by LovetoKnow. <http://exercise.lovetoknow.com/Examples_of_Interval_Training>.

USDA. "The Food Guide Pyramid." Published Aug. 1992 by USDA.

Golo, LLC, "Golo for Life: Creating Matrix Meals (TM)" [Brochure], (May 2013).

Uauy et al., WHO/FAO release independent Expert Report on diet and chronic disease: Less saturated fats, sugar and salt, more fruits and vegetables and physical exercise, needed to counter cardiovascular diseases, cancer, diabetes and obesity,? Released Mar. 3, 2003.

U.S. Appl. No. 61/869,047, filed Aug. 22, 2013.

Coffman, Healthy Eating: Daily Amounts of Carbs, Fats, Fiber, Sodium & Protein,? published online by at least Jul. 23, 2013 at <https://web>.archive.org/web/20130725003302/http://healthyeating.sfgate.com/daily-amounts-carbs-fat-fiber-sodium-protein-4230.html.

Abstract article for WO201502990 filed Jul. 1, 2014.

Ballantyne, Weight-Loss Winner: A Diet High in Fiber, Low in Calories,? Scien. Amer. (Apr. 25, 2009).

International Preliminary Report on Patentability in International Application No. PCT/IB2015/001299 dated Nov. 11, 2016.

Palo Alto Medical Foundation. "Balance Your Meals". Published Oct. 13, 2008. <https://web/archive.org/web/20081O13044837/http://www.pamf.org/southasian/healthy/nutrition/balance.html>.

Albemarle Regional Health Services. "Activity Conversion Chart". Jan. 11, 2011. <https://www.arhs-nc.org/livehealthy/data/StepConversionChart.pdf>.

\* cited by examiner

FORMULATIONS FOR WEIGHT LOSS AND METHODS OF USE

PRIORITY PARAGRAPH

This application is a continuation of U.S. application Ser. No. 17/139,141, filed on Dec. 31, 2020, which is a continuation of U.S. application Ser. No. 16/868,918, filed on May 7, 2020, which is a continuation of U.S. application Ser. No. 15/887,666, filed on Feb. 2, 2018, now U.S. Pat. No. 10,765,718 issued on Sep. 8, 2020, which claims priority to U.S. Provisional Application No. 62/453,890, filed on Feb. 2, 2017, titled, "Formulations For Weight Loss and Methods of Use", each of which are incorporated herein by reference in their entireties.

SUMMARY

Embodiments herein are directed to a weight loss composition including banaba leaf extract, *rhodiola* root extract, apple fruit extract, zinc, and magnesium. In some embodiments, the zinc and/or magnesium are in chelated form. In some embodiments, the weight loss composition comprises banaba leaf extract in an amount of about 10 mg to about 100 mg, apple fruit extract in an amount greater than about 30 mg, *Rhodiola* root extract in an amount of about 140 mg to about 500 mg, magnesium in an amount of about 10 mg to about 75 mg, and zinc in an amount greater than about 15 mg. In some embodiments, the zinc and/or magnesium are in chelated form. In some embodiments, the weight loss composition may further comprise at least one of the following: chromium chelate, *gardenia* fruit extract, *salacia* extract, inositol, and berberine hydrochloride.

Some embodiments are directed to a method for promoting weight loss in a subject comprising administering to the subject a weight loss composition including banaba leaf extract, *rhodiola* root extract, apple fruit extract, zinc, and magnesium. In some embodiments, the zinc and/or magnesium are in chelated form. Some embodiments are directed to a method of treating or preventing obesity in a subject comprising administering to the subject a weight loss composition including banaba leaf extract, *rhodiola* root extract, apple fruit extract, zinc, and magnesium. In some embodiments, the zinc and/or magnesium are in chelated form. Some embodiments are directed to a method of improving insulin resistance in a subject comprising administering to the subject a weight loss composition including banaba leaf extract, *rhodiola* root extract, apple fruit extract, zinc, and magnesium. In some embodiments, the zinc and/or magnesium are in chelated form.

Some embodiments are directed to a method for promoting weight loss in a subject comprising administering to the subject a weight loss composition including banaba leaf extract, *rhodiola* root extract, apple fruit extract, zinc, and magnesium. In some embodiments, the zinc and/or magnesium are in chelated form. Some embodiments are directed to a method for promoting weight loss in a subject in need thereof comprising administering to the subject a weight loss composition including banaba leaf extract, *rhodiola* root extract, apple fruit extract, zinc, and magnesium, wherein the subject is following a weight management plan designed to stabilize and optimize insulin levels. In some embodiments, the zinc and/or magnesium are in chelated form. Some embodiments are directed to a method for promoting weight loss in a subject in need thereof comprising administering to the subject a weight loss composition including banaba leaf extract, *rhodiola* root extract, apple fruit extract, zinc, and magnesium; and a bulk food product of embodiments herein, wherein the subject is following a weight management plan of embodiments herein designed to stabilize and optimize insulin levels. In some embodiments, the zinc and/or magnesium are in chelated form.

Some embodiments are directed to a method of treating or preventing obesity in a subject comprising administering to the subject a weight loss composition including banaba leaf extract, *rhodiola* root extract, apple fruit extract, zinc and magnesium; and a bulk food product of embodiments herein. Some embodiments are directed to a method of treating or preventing obesity in a subject in need thereof comprising administering to the subject a weight loss composition including banaba leaf extract, *rhodiola* root extract, apple fruit extract, zinc and magnesium, wherein the subject is following a weight management plan designed to stabilize and optimize insulin levels. Some embodiments are directed to a method of treating or preventing obesity in a subject in need thereof comprising administering to the subject a weight loss composition including banaba leaf extract, *rhodiola* root extract, apple fruit extract, zinc and magnesium; and a bulk food product of embodiments herein, wherein the subject is following a weight management plan of embodiments herein designed to stabilize and optimize insulin levels.

Some embodiments are directed to a method of improving insulin resistance in a subject comprising administering to the subject a weight loss composition including banaba leaf extract, *rhodiola* root extract, apple fruit extract, zinc and magnesium; and a bulk food product of embodiments herein. Some embodiments are directed to a method of improving insulin resistance in a subject in need thereof comprising administering to the subject a weight loss composition including banaba leaf extract, *rhodiola* root extract, apple fruit extract, zinc and magnesium, wherein the subject is following a weight management plan designed to stabilize and optimize insulin levels. Some embodiments are directed to a method of improving insulin resistance in a subject in need thereof comprising administering to the subject a weight loss composition including banaba leaf extract, *rhodiola* root extract, apple fruit extract, zinc and magnesium; and a bulk food product of embodiments herein, wherein the subject is following a weight management plan of embodiments herein designed to stabilize and optimize insulin levels.

Some embodiments are directed to a kit comprising a weight loss composition comprising banaba leaf extract, *rhodiola* root extract, apple fruit extract, zinc and magnesium, and instructions for a weight management plan designed to stabilize and optimize insulin levels.

Some embodiments are directed to a kit comprising a weight loss composition comprising banaba leaf extract, *rhodiola* root extract, apple fruit extract, zinc and magnesium, and a bulk food product comprising protein, fat, carbohydrates, fiber and a phyto blend of at least two of the following: mushroom powder, moringa leaf extract, ginger, turmeric, saffron, a natural supplement blend, digestive enzymes, probiotics (e.g. *Bacillus subtilis*, such as that sold under the tradename DE111™, or *B. coagulans*, such as that sold under the tradename LactoSpore™), fruits, vegetables, and herbs. In some embodiments, the ginger may be ginger rhizome. In some embodiments, the turmeric may be turmeric rhizome.

Some embodiments are directed to a kit comprising a weight loss composition comprising banaba leaf extract, *rhodiola* root extract, apple fruit extract, zinc and magnesium, a weight management plan designed to stabilize and optimize insulin levels, and a bulk food product.

DETAILED DESCRIPTION

Figure 1:
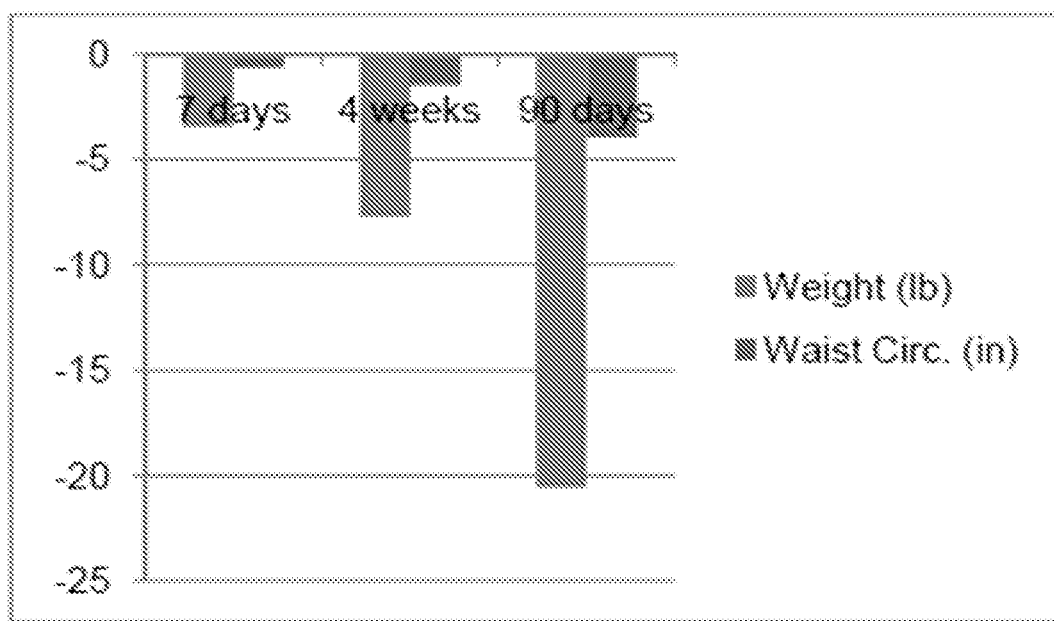
FIG. 1 illustrates change in average body weight (lb) and waist circumference after 7 days, 30 days and 90 days.

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

As used herein and in the appended claims, the singular forms "a", "an", and "the" include plural reference unless the context clearly dictates otherwise. Thus, for example, reference to an "antioxidant" is a reference to one or more antioxidants and equivalents thereof known to those skilled in the art, and so forth.

As used herein, the term "about" means plus or minus 10% of the numerical value of the number with which it is being used. Therefore, about 50% means in the range of 45%-55%.

As used herein, the term "weight management" refers to weight loss, weight gain or weight maintenance, according to the desired effect.

As used herein, the term "weight loss" refers to weight loss as well as weight maintenance.

"Administering" when used in conjunction with a therapeutic means to administer a therapeutic to a patient whereby the therapeutic positively impacts the tissue to which it is targeted. Thus, as used herein, the term "administering", when used in conjunction with a weight loss composition, can include, but is not limited to, oral or parenteral administration. Suitable forms for the weight loss composition for oral or parenteral administration may include tablets, softgels, capsules, lozenges, syrups, granules, solutions and suspensions which contain unit doses of the supplement for administration once or several times a day. The weight loss composition of the invention may typically be administered orally as a tablet or a capsule. Tablets, softgels, gel tabs, capsules, liquid and sustained release formulations may be formulated and prepared according to manufacturing techniques well known in the pharmaceutical industry and in a variety of dosage forms "Administering" a composition may be accomplished by oral administration, parenteral administration, or by either method in combination with other known techniques.

The term "animal," "patient," or "subject" as used herein includes, but is not limited to, humans and non-human vertebrates such as wild, domestic and farm animals. Preferably, the term refers to humans.

The term "inhibiting" includes the administration of a compound of the present invention to prevent the onset of the symptoms, alleviate the symptoms, not worsen the symptoms or eliminate the disease, condition, disorder or a symptom or symptoms thereof.

By "pharmaceutically acceptable", it is meant the carrier, diluent or excipient must be compatible with the other ingredients of the formulation and not deleterious to the recipient thereof.

As used herein, the term "therapeutic" means an agent utilized to discourage, combat, ameliorate, prevent or improve an unwanted condition, disease or symptom of a patient. In part, embodiments of the present disclosure are directed to promoting weight loss, treating and preventing obesity and obesity related conditions.

A "therapeutically effective amount" or "effective amount" of a composition is a predetermined amount calculated to achieve the desired effect, i.e., to supplement, promote, or increase nutritional health. The activity contemplated by the present methods includes both therapeutic and/or prophylactic treatment, as appropriate. The specific dose administered according to this disclosure to obtain therapeutic and/or prophylactic effects will, of course, be determined by the particular circumstances surrounding the case, including, for example, the formulation administered, the route of administration, and the condition (e.g. weight loss, weight gain, weight management, obesity, insulin resistance) being treated. In some embodiments, the effective amount administered may be determined by the physician in the light of the relevant circumstances including the condition to be treated, the choice of compound to be administered, and the chosen route of administration. A therapeutically effective amount of compound of this invention is typically an amount such that when it is administered in a physiologically tolerable excipient composition, it is sufficient to achieve an effective systemic concentration or local concentration in the target tissue.

The terms "ameliorate," "improve," or "promote" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms of the condition, disorder or disease; diminishment of the extent of the condition, disorder or disease; stabilization (i.e., not worsening) of the state of the condition, disorder or disease; maintain the condition, disorder or disease; delay in onset or slowing of the progression of the condition, disorder or disease; and remission (whether partial or total), whether detectable or undetectable, or enhancement or improvement of the condition, disorder or disease. Examples of beneficial or desired clinical results may include, without limitation, treatment and alleviation of insulin resistance, treatment of obesity, reduction in weight, prevention of weight gain, fat loss, reduction of hunger and cravings, and stabilization and optimization of insulin levels. The terms may further be used to convey that the disease or condition is not worsened by administration of the weight loss composition of embodiments herein. Amelioration or promotion includes eliciting a clinically significant response without excessive levels of side effects.

In embodiments or claims where the term "comprising" is used as the transition phrase, such embodiments can also be envisioned with replacement of the term "comprising" with the terms "consisting of" or "consisting essentially of."

As used herein, the term "consists of" or "consisting of" means that the formulation includes only the elements, steps, or ingredients specifically recited in the particular claimed embodiment or claim.

As used herein, the term "consisting essentially of" or "consists essentially of" means that the only active ingredient(s) in the formulation or method that treats the specified condition (e.g. nutrient depletion) is the specifically recited therapeutic(s) in the particular embodiment or claim.

In some aspects, the invention is directed to a weight loss composition as disclosed in embodiments below, or an effective amount of a weight loss composition, as disclosed in embodiments below.

This application relates generally to weight loss and, more particularly, to methods and systems of administering weight loss programs. Obesity is a significant health risk and can cause and/or contribute to a number of obesity-related conditions, such as hypertension, lipid disease, type two diabetes, cancer, orthopedic conditions, and other diseases. The treatment of such obesity-related conditions can often be expensive over the course of the person's life.

Treatment of obese or overweight individuals can include improved diet and physical exercise. However, efforts to diet and exercise are not successful for everyone. Sedentary lifestyles, ready availability of poor dietary choices, genetic risk factors, and stress all can make it difficult to lose unwanted weight. Medication has offered avenues to lose weight by, for example, reducing the absorption of fat that has been ingested in the diet. However, drug treatments may only result in modest weight reduction, can include deleterious side effects, and may not have a beneficial effect on the long-term issues related to increased weight e.g., diabetes, cardiovascular disease, etc.

Some individuals opt for surgery to lose weight by, for example, reducing the size of the stomach or reducing the length of the bowels. However, complications from surgery are frequent and behavior modification is needed to enhance the likelihood of a successful outcome.

Weight loss compositions are one method of weight reduction used by individuals regardless of weight classification. Numerous types of supplements exist affecting different factors related to weight loss. Certain supplements are aimed at, for example, appetite suppression, decreased nutrient absorption, or increased metabolism. However, these supplements often pose potential problems and harmful side effects of their own. Supplements intended for reducing appetite may not work as intended because the neural basis of appetite is not fully understood. Supplements for blocking absorption of dietary fats may cause oily stools, stomach pain, and flatulence. Supplements containing active ingredients that stimulate the central nervous system can carry a risk of high blood pressure, faster heart rate, palpitations, closed-angle glaucoma, drug addiction, restlessness, agitation, and insomnia.

There is thus a great need for a weight loss composition that facilitates fat burning and/or weight loss, while decreasing the side effects known to be associated with other weight loss methods and compositions. Additionally, there is a need for a weight loss composition that will take a more holistic approach to weight loss, targeting different obesity promoting mechanisms, to achieve a synergistic weight loss effect in subjects.

Some embodiments herein are directed to a weight loss composition that includes a mood enhancer, an insulin sparing agent, and a peripheral energy blocker. It is believed that the use of a mood enhancer, included in a weight loss program, may increase endurance and diminish fatigue as well as a heighten the sense of emotional and mental wellbeing, which would help a subject be more inclined to begin, and adhere to, an exercise and diet program. A peripheral energy blocker, included in embodiments herein, is believed to prevent the digestion of excess fat and refined carbohydrates in the diet, thereby allowing it to pass through their systems without getting absorbed. The use of an insulin sparing agent in a weight loss program may help to lower insulin levels. Insulin has several different effects that lead to fat accumulation in adipose tissue. For example, insulin: (1) promotes fat synthesis; (2) increases the utilization of glucose, which automatically decreases the utilization of fat; (3) inhibits the action of hormone-sensitive lipase, thereby preventing break down of fat and promoting fat storage.

Fat cells have historically been accredited with two main functions, namely that of storing energy and preserving body temperature via insulation. In the presence of excess intra-abdominal (visceral) fat, however, fat cells, once filled with fat, also assume a hormonal function by manufacturing and releasing various chemical substances called inflammatory cytokines, able to mimic or interfere with normal hormonal functions. For reasons not completely understood, some of these inflammatory cytokines disrupt insulin's role on cellular level (at the insulin receptor that regulates the glucose portal across the cell membrane) and render insulin less effective. The medical term for this condition is 'insulin resistance'. To get the same task done as before, the body compensates by producing even more insulin, and insulin levels rise above the norm.

Because of insulin's obesity-promoting effects, insulin resistance makes one more prone to gaining weight than before. In addition, it also makes it more difficult for one to lose weight. Once this condition sets in, a vicious cycle begins, explaining why many obese individuals, once burdened with excess visceral fat, experience that their metabolism has effectively slowed down.

It is believed that fat breakdown and use of fat to provide energy are enhanced in the absence of insulin. This can occur normally between meals when secretion of insulin is minimal but the effect becomes extreme in diabetes mellitus when secretion of insulin, is almost absent. When this happens, the aforementioned effects of insulin causing the production and storage of fat, are reversed. A dominant effect is that the enzyme hormone-sensitive lipase in the fat cells becomes strongly activated. This causes hydrolysis of stored triglycerides, releasing large quantities of fatty acids and glycerol from the adipose tissue into the circulating blood. The net effect is significant weight-loss.

Weight Loss Composition

The weight loss composition of embodiments herein are a combination of naturally derived plant extracts that display complementary and synergistic pharmaceutical effects as well as minerals, all of which result in the treatment or alleviation of insulin resistance, and optimization of catabolic metabolism by lowering insulin levels and increasing the usage of fat for energy purposes, thereby assisting with weight loss.

Some embodiments herein are directed to a weight loss composition comprising a *Rhodiola* root extract, a banaba leaf extract, and an apple fruit extract. In some embodiments, the weight loss composition may further include at least one or more of the following: zinc, magnesium, berberine, inositol, *Salacia* extract, *gardenia* fruit extract, and chromium. In some embodiments, the zinc, magnesium, and/or chromium are in chelated form.

In some embodiments, the *Rhodiola* root extract may include rosavin, rosarian, rosin, and salidroside. In some embodiments, the *Rhodiola* root extract could be derived from *Rhodiola rosea*. In some embodiments, the weight loss composition may comprise rosavin in an amount of up to about 5%, up to about 4%, up to about 3%, or a value within these ranges. In some embodiments, the weight loss composition may comprise salidroside in an amount of up to about 2%, up to 1%, or a value within these ranges. In some embodiments, the *Rhodiola* root extract is in an amount of about 100 mg/day to about 500 mg/day, about 100 mg/day to about 400 mg/day, about 100 mg/day to about 350 mg/day, about 100 mg/day to about 340 mg/day, about 140 mg/day to about 500 mg/day, about 140 mg/day to about 400 mg/day, about 140 mg/day to about 350 mg/day, about 140 mg/day to about 340 mg/day, about 200 mg/day to about to about 500 mg/day, about 200 mg/day to about 400 mg/day, about 200 mg/day to about 350 mg/day, about 200 mg/day to about 340 mg/day, about 300 mg/day to about to about 500 mg/day, about 300 mg/day to about 400 mg/day, about 300 mg/day to about 350 mg/day, about 300 mg/day to about 340 mg/day, or a value within any of these ranges. In some embodiments, the *Rhodiola* root extract is in an amount of about 140 mg/day, about 150 mg/day, about 200 mg/day, about 300 mg/day, about 340 mg/day, about 350 mg/day, about 400 mg/day, about 500 mg/day, or a range between any two of these values.

In some embodiments, the banaba leaf extract may be derived from *Lagerstroemia speciosa*. In some embodiments, the banaba leaf extract may comprise corosolic acid. In some embodiments, the weight loss composition may comprise corosolic acid rather than banaba leaf extract. In some embodiments, the corosolic acid (either in the banaba leaf extract or as an ingredient of the weight loss composition) may be in an amount of greater than about 2%, about 2% to about 30%, about 2% to about 25%, about 2% to about 20%, about 2% to about 18%. In some embodiments, the corosolic acid (either in the banaba leaf extract or as an ingredient of the weight loss composition) may be in an amount of about 2%, about 5%, about 10%, about 15%, to about 20%, about 25%, about 16%, about 17%, about 18%, or a range between any two of these values. In some embodiments, the corosolic acid may be in an amount of about 5 mg/day to about 50 mg/day, about 5 mg/day to about 40 mg/day, about 5 mg/day to about 30 mg/day, about 5 mg/day to about 20 mg/day, about 5 mg/day to about 10 mg/day, about 10 mg/day to about 50 mg/day, about 10 mg/day to about 40 mg/day, about 10 mg/day to about 30 mg/day, about 10 mg/day to about 20 mg/day, or a value within this range. In some embodiments, the corosolic acid may be in an amount selected from about 5 mg/day, about 10 mg/day, about 15 mg/day, about 20 mg/day, or a range between any two of these values. In some embodiments, the banaba leaf extract may be in an amount of about 10 mg/day to about 100 mg/day, about 10 mg/day to about 75 mg/day, about 10 mg/day to about 60 mg/day, about 20 mg/day to about 100 mg/day, about 20 mg/day to about 75 mg/day, about 20 mg/day to about 60 mg/day, about 40 mg/day to about 100 mg/day, about 40 mg/day to about 75 mg/day, about 40 mg/day to about 60 mg/day, or a value within these ranges. In some embodiments, the banaba leaf extract may be in an amount of about 10 mg/day, about 20 mg/day, about 30 mg/day, about 40 mg/day, about 56 mg/day, about 60 mg/day, about 75 mg/day, about 100 mg/day, or a range between any two of these values.

In some embodiments, the apple fruit extract may be derived from *Malus domestica*. In some embodiments, the apple fruit extract may include greater than about 30% polyphenols, about 30% to about 99% polyphenols, about 30% to about 90% polyphenols, about 30% to about 80% polyphenols, about 30% to about 75% polyphenols, about 40% to about 90% polyphenols, about 40% to about 80% polyphenols, about 40% to about 75% polyphenols, about 50% to about 90% polyphenols, about 50% to about 80% polyphenols, about 50% to about 75% polyphenols, or a value within any of these ranges. In some embodiments, the apple fruit extract may include polyphenols in an amount of about 30%, about 40%, about 50%, about 60%, about 75%, about 80%, about 90%, about 99%, or a range between any two of these values. The apple fruit extract may be in an amount greater than 30 mg/day, about 30 mg/day to about 100 mg/day, about 30 mg/day to about 75 mg/day, about 30 mg/day to about 50 mg/day, about 30 mg/day to about 45 mg/day, about 40 mg/day to about 100 mg/day, about 40 mg/day to about 75 mg/day, about 40 mg/day to about 50 mg/day, about 40 mg/day to about 45 mg/day, or a value within any of these ranges. In some embodiments, the apple fruit extract may be in an amount of about 35 mg/day, about 40 mg/day, about 45 mg/day, about 50 mg/day, about 60 mg/day, about 70 mg/day, about 80 mg/day, about 90 mg/day, about 100 mg/day, or a range between any two of these values.

In some embodiments, the zinc may be in a chelated form, for example, as zinc biglycinate chelate, zinc gluconate, zinc citrate, zinc picolinate, zinc methionate, zinc orotate, or the like. In some embodiments, the zinc chelate is zinc biglycinate chelate, such as that sold under the trade name TRAACS®. In some embodiments, the elemental zinc may be in an amount greater than about 15 mg/day, about 5 mg/day to about 40 mg/day. In some embodiments, the elemental zinc may be in an amount of about 5 mg/day to about 35 mg/day, about 5 mg/day to about 30 mg/day, about 10 mg/day to about 50 mg/day, about 10 mg/day to about 45 mg/day, about 10 mg/day to about 40 mg/day, about 10 mg/day to about 35 mg/day, about 10 mg/day to about 30 mg/day, or a value between any of these ranges. In some embodiments, the elemental zinc may be in an amount of about 5 mg/day, about 10 mg/day, about 15 mg/day, about 20 mg/day, about 25 mg/day, about 30 mg/day, about 35 mg/day, about 40 mg/day, or a range between any two of these values.

In some embodiments, the magnesium may be in a chelated form, for example, as magnesium glycinate, magnesium malate, magnesium taurate, magnesium orotate, magnesium lysinate, dimagnesium malate, or the like. In some embodiments, the magnesium may be dimagnesium malate, such as that sold under the trade name Albion®. In some embodiments, the elemental magnesium may be in an amount of about 5 mg/day to about 100 mg/day, about 5 mg/day to about 75 mg/day, about 5 mg/day to about 50 mg/day, about 5 mg/day to about 45 mg/day, about 10 mg/day to about 100 mg/day, about 10 mg/day to about 75 mg/day, about 10 mg/day to about 50 mg/day, about 10 mg/day to about 45 mg/day, or a value between any of these ranges. In some embodiments, the elemental magnesium may be in an amount of about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 55 mg/day, about 60 mg/day, about 65 mg/day, about 70 mg/day, about 75 mg/day, about 80 mg/day, about 90 mg/day, about 100 mg/day, or a range between any two of these values.

In some embodiments, the chromium may be in a chelated form, such as chromium glycinate, chromium nicotinate, chromium nicotinate glycinate, chromium picolinate, chromium GTF (glucose tolerance factor) chelate, chromium polynicotinate, or the like. In some embodiments, the chromium may be chromium nicotinate glycinate, such as that sold under the trade name TRAACS®. In some embodiments, the elemental chromium may be in an amount of about 100 mcg/day to about 300 mcg/day, about 100 mcg/day to about 250 mcg/day, about 100 mcg/day to about 210 mcg/day, about 125 mcg/day to about 300 mcg/day, about 125 mcg/day to about 250 mcg/day, about 125 mcg/day to about 210 mcg/day, about 150 mcg/day to about 300 mcg/day, about 150 mcg/day to about 250 mcg/day, about 150 mcg/day to about 210 mcg/day, about 175 mcg/day to about 300 mcg/day, about 175 mcg/day to about 250 mcg/day, about 175 mcg/day to about 210 mcg/day, about 200 mcg/day to about 300 mcg/day, about 200 mcg/day to about 250 mcg/day, about 200 mcg/day to about 210 mcg/day, or a value within one of these ranges. In some embodiments, the elemental chromium may be in an amount of about 300 mcg/day, about 250 mcg/day, about 210 mcg/day, about 175 mcg/day, about 150 mcg/day, about 125 mcg/day, about 100 mcg/day, or a range between any two of these values.

In some embodiments, the *Salacia* extract may be derived from *Salacia reticulata*, such as that sold under the trade name Salaretin®. In some embodiments, the *Salacia* extract may be *Salacia* bark extract, *Salacia* root extract, *Salacia* stem extract, or a combination thereof. In some embodiments, the *Salacia* extract may have an extract ratio of 20:1, 15:1, 10:1, 6:1, 5:1, 4:1, or the like. In some embodiments, the *Salacia* extract may have an extract ratio of 6:1. In some embodiments, the *Salacia* extract may be in an amount of about 10 mg/day to about 400 mg/day. In some embodiments, the *Salacia* extract may be in an amount of about 10 mg/day to about 300 mg/day, about 10 mg/day to about 200 mg/day, about 10 mg/day to about 100 mg/day, about 10 mg/day to about 75 mg/day, about 10 mg/day to about 70 mg/day, about 10 mg/day to about 65 mg/day, about 10 mg/day to about 60 mg/day, about 10 mg/day to about 55 mg/day, about 10 mg/day to about 50 mg/day, about 10 mg/day to about 45 mg/day, about 20 mg/day to about 100 mg/day, about 20 mg/day to about 75 mg/day, about 20 mg/day to about 50 mg/day, about 20 mg/day to about 45 mg/day, or a value selected therefrom. In some embodiments, the *Salacia* extract may be in an amount of about 10 mg/day, about 20 mg/day, about 30 mg/day, about 35 mg/day, about 40 mg/day, about 45 mg/day, about 50 mg/day, about 55 mg/day, about 60 mg/day, about 70 mg/day, about 75 mg/day, about 80 mg/day, about 90 mg/day, about 100 mg/day, about 150 mg/day, about 200 mg/day, about 250 mg/day, about 300 mg/day, about 350 mg/day, about 400 mg/day, or a range between any two of these values.

In some embodiments, the berberine may be berberine hydrochloride. In some embodiments, the berberine may be derived from Barberry bark and root extract. In some embodiments, the berberine may be derived from *Berberis vulgaris*. In some embodiments, the berberine may be derived from *Berberis vulgaris, Hydrastis canadensis, Coptis chinensis, Phellodendron amurense, Berberis aristata* or a combination thereof. In some embodiments, the berberine may be in an amount of about 50 mg/day to about 200 mg/day, about 50 mg/day to about 150 mg/day, about 50 mg/day to about 125 mg/day, about 50 mg/day to about 105 mg/day, about 75 mg/day to about 200 mg/day, about 75 mg/day to about 150 mg/day, about 75 mg/day to about 125 mg/day, about 75 mg/day to about 105 mg/day, about 100 mg/day to about 200 mg/day, about 100 mg/day to about 150 mg/day, about 100 mg/day to about 125 mg/day, about 100 mg/day to about 105 mg/day, or a value within any of these ranges. In some embodiments, the berberine may be in an amount of about 50 mg/day, about 75 mg/day, about 100 mg/day, about 105 mg/day, about 115 mg/day, about 125 mg/day, about 150 mg/day, about 200 mg/day, or a range between any two of these values.

Inositol occurs naturally as phytic acid in the fiber component of certain plant foods, and as myo-inositol in meat. In some embodiments, the inositol may be naturally derived. In some embodiments, the inositol may be manufactured synthetically. It is believed that inositol increases the action of insulin by improving insulin sensitivity. In some embodiments, the inositol is in an amount of about 100 mg/day to about 300 mg/day, about 100 mg/day to about 250 mg/day, about 100 mg/day to about 210 mg/day, about 125 mg/day to about 300 mg/day, about 125 mg/day to about 250 mg/day, about 125 mg/day to about 210 mg/day, about 150 mg/day to about 300 mg/day, about 150 mg/day to about 250 mg/day, about 150 mg/day to about 210 mg/day, about 175 mg/day to about 300 mg/day, about 175 mg/day to about 250 mg/day, about 175 mg/day to about 210 mg/day, about 200 mg/day to about 300 mg/day, about 200 mg/day to about 250 mg/day, about 200 mg/day to about 210 mg/day, or a value within one of these ranges. In some embodiments, the inositol may be in an amount of about 300 mg/day, about 250 mg/day, about 210 mg/day, about 175 mg/day, about 150 mg/day, about 125 mg/day, about 100 mg/day, or a range between any two of these values.

In some embodiments, the *gardenia* fruit extract is derived from *Gardenia jasminoides*. In some embodiments, the *gardenia* fruit extract may have an extract ratio of 20:1, 15:1, 10:1, 6:1, 5:1, 4:1, or the like. In some embodiments, the *gardenia* fruit extract may have an extract ratio of 10:1. In some embodiments, the *gardenia* fruit extract is in an amount of about 25 mg/day to about 200 mg/day, about 25 mg/day to about 150 mg/day, about 25 mg/day to about 100 mg/day, about 25 mg/day to about 90 mg/day, about 50 mg/day to about 200 mg/day, about 50 mg/day to about 150 mg/day, about 50 mg/day to about 100 mg/day, about 50 mg/day to about 90 mg/day, or a value within any of these ranges. In some embodiments, the *gardenia* fruit extract is in an amount of about 25 mg/day, about 50 mg/day, about 75 mg/day, about 90 mg/day, about 100 mg/day, about 125 mg/day, about 150 mg/day, about 175 mg/day, about 200 mg/day, or a range between any two of these values.

In some embodiments, the weight loss composition comprises banaba leaf extract, apple fruit extract, *Rhodiola* root extract, magnesium chelate, and zinc chelate. In some embodiments, the weight loss composition comprises banaba leaf extract, apple fruit extract, *Rhodiola* root extract, *gardenia* fruit extract, inositol, berberine hydrochloride, *Salacia* extract, magnesium chelate, zinc chelate, and chromium. In some embodiments, the weight loss composition consists essentially of banaba leaf extract, apple fruit extract, *Rhodiola* root extract, *gardenia* fruit extract, inositol, berberine hydrochloride, *Salacia* extract, magnesium chelate, zinc chelate, and chromium. In some embodiments, the weight loss composition consists of banaba leaf extract, apple fruit extract, *Rhodiola* root extract, *gardenia* fruit extract, inositol, berberine hydrochloride, *Salacia* extract, magnesium chelate, zinc chelate, and chromium.

In some embodiments, the weight loss composition comprises banaba leaf extract in an amount of about 10 mg/day to about 100 mg/day, apple fruit extract in an amount greater than about 30 mg/day, *Rhodiola* root extract in an amount of about 140 mg/day to about 500 mg/day, magnesium chelate in an amount of about 10 mg/day to about 75 mg/day, and zinc chelate in an amount greater than about 15 mg/day. In some embodiments, the weight loss composition comprises banaba leaf extract in an amount of about 56 mg/day, apple fruit extract in an amount of about 45 mg/day, *Rhodiola* root extract in an amount of about 340 mg/day, magnesium chelate in an amount of about 45 mg/day, and zinc chelate in an amount of about 30 mg/day. In some embodiments, the weight loss composition comprises banaba leaf extract in an amount of about 56 mg/day, apple fruit extract in an amount of about 45 mg/day, *Rhodiola* root extract in an amount of about 340 mg/day, magnesium chelate in an amount of about 45 mg/day, zinc chelate in an amount of about 30 mg/day, berberine hydrochloride in an amount of about 105 mg/day, inositol in an amount of about 210 mg/day, *Salacia* extract in an amount of about 45 mg/day, *gardenia* fruit extract in an amount of about 90 mg/day, and chromium chelate in an amount of about 210 mcg/day. In some embodiments, the weight loss composition consists essentially of banaba leaf extract in an amount of about 56 mg/day, apple fruit extract in an amount of about 45 mg/day, *Rhodiola* root extract in an amount of about 340 mg/day, magnesium chelate in an amount of about 45 mg/day, zinc chelate in an amount of about 30 mg/day, berberine hydrochloride in an amount of about 105 mg/day, inositol in an amount of about 210 mg/day, *Salacia* extract in an amount of about 45 mg/day, *gardenia* fruit extract in an amount of about 90 mg/day, and chromium chelate in an amount of about 210 mcg/day. In some embodiments, the apple fruit extract includes about 75% polyphenols. In some embodiments, the weight loss composition consists of banaba leaf extract in an amount of about 56 mg/day, apple fruit extract in an amount of about 45 mg/day, *Rhodiola* root extract in an amount of about 340 mg/day, magnesium chelate in an amount of about 45 mg/day, zinc chelate in an amount of about 30 mg/day, berberine hydrochloride in an amount of about 105 mg/day, inositol in an amount of about 210 mg/day, *Salacia* extract in an amount of about 45 mg/day, *gardenia* fruit extract in an amount of about 90 mg/day, and chromium chelate in an amount of about 210 mcg/day.

While the amounts of ingredients above have been given in mass units per day, it is conceivable that a weight loss composition may comprise the recited mass units to administered in one unit dosage taken once daily or divided into multiple unit dosages.

Weight Management Plan

Some embodiments herein are directed to a kit comprising the weight loss compositions of embodiments herein and instructions for a weight management plan. In some embodiments, the instructions may be in the form of a website address, a mobile app, a brochure, chart, a booklet, a combination thereof, or the like. The weight management plan of embodiments herein focuses on whole foods and on feeding the body nutritious foods which are low in preservatives and additives and which are not necessarily low in fat or calories. The intention is to control satiety and to sustain energy while energizing the metabolism. The weight management plan of embodiments herein are also designed to ensure that a subject consumes balanced meals which include food selected from each food category i.e. protein, fat, carbohydrates (such as from starches and fruit), and vegetables to optimize insulin effects and to maximize energy while causing the body to burn fat without any meaningful muscle loss. In some embodiments, the weight management plan comprises:

(1) establishing a food index which includes four main categories of food, namely vegetables, proteins, carbohydrates (including from starches and fruit), and fat, defining a portion for each category and assigning a food value to each respective portion, in units, wherein the food value is based, at least, on the following parameters: calories, sugar content, fiber content, fat content, and processed content (including additives and processed sugars);

(2) determining a subject's base food allowance, in terms of the units, based at least on one or more of the following parameters of the subject:
  gender;
  age;
  height;
  BMI;
  weight; and
  life activity;

(3) establishing an activity index, which includes a variety of exercises that could be performed by a subject, defined in terms of a time interval for which the exercise is performed, and assigning a value, in the units, to each time interval;

(4) determining, for the subject, a daily food allowance, in the units, as the sum of the base food allowance and values obtained from the activity index due to corresponding activities that are listed in the activity index being performed by the subject, and (5) allowing the subject to choose, from the food index, portions of foods for consumption, wherein the sum of the food values of the chosen portions of foods is in a predetermined relationship to the daily food allowance. In some embodiments, the sum of the food values of the chosen portion of food should not vary from the daily food allowance by more than 10%. In some embodiments, at least one food portion is selected from each food category for each meal; and at least three meals are consumed each day.

The following formula may be used to provide a rough estimate of a particular food's food value: for a given amount of food, i.e. a portion expressed in a conventional measurement unit (e.g. a cup, an ounce, a tablespoon, milliliters, grams, or the like), the following assessments are made:
  a base energy value (B) is determined by dividing the calorie value of the food portion by a factor of 2.7 to 3;
  the following values are established in grams;
    a. fiber content (F);
    b. protein content (P);
    c. sugar content (S);
    d. fat content (FT); and
    e. processed content (PC).

The food value for the chosen portion is established by subtracting the positive values items (fiber and protein) from the base energy value and by adding the negative value items (sugar, fat and processed content) to the base energy value, as follows:

$$B-F-P+S+FT+PC=FV$$

The subject's base food allowance, determined in step (2), is preferably linked to the quantity of food a subject can consume each day, before exercise, to lose between one and two pounds of fat weight per week.

The food categories used in the weight management plan may include vegetables, protein, carbohydrates (which includes starches and fruit) and fat. The plan requires the inclusion of at least one portion of each food group in each meal and promotes the consumption of three meals a day using all four food groups, with snacks, as may be appropriate.

As an example, a single bagel and a glass of orange juice equate to 300 food value units, and represent approximately one and a half times the glucose and insulin loads which would be created by the consumption of two eggs, a slice of toast, a ½ cup of fruit, a cup of vegetables and one teaspoon of real butter (±175 food value units).

A subject who ate the bagel and juice would have an insulin spike which results in an increase in fat storage but there would be no protein or fat consumption. Energy levels would rapidly decline within about two hours resulting in a reduction in the metabolism rate and this would create a need for food and sugar. The alternative food consumption proposed by embodiments of the weight management plan would allow the subject to produce less glucose and insulin. Excess glucose would not be stored as fat. In response to the ingestion of the alternative foods (eggs, toast, fruit etc.) the body would accelerate the metabolic rate, and would seek energy reserves from stored food. Satiety and high energy levels would be maintained for three to four hours or until legitimate hunger pangs again arose.

In some embodiments, the weight loss composition is designed to be taken with a meal. In some embodiments, the weight loss composition is designed to be taken before a meal. In some embodiments, the weight loss composition is designed to be taken before a meal by about 15 minutes to about 120 minutes, about 15 minutes to about 90 minutes, about 15 minutes to about 60 minutes, about 15 minutes to about 45 minutes, about 15 minutes to about 30 minutes, about 30 minutes to about 120 minutes, about 30 minutes to about 90 minutes, about 30 minutes to about 60 minutes, about 30 minutes to about 45 minutes, or a value within any of these ranges.

Bulk Food Product

Some embodiments herein are directed to a bulk food product. Some embodiments herein are directed to a kit comprising a bulk food product of embodiments herein and the weight loss composition of embodiments herein. Embodiments are also directed to a kit comprising the bulk food product of embodiments herein, instructions for the weight loss plan of embodiments herein, and the weight loss composition of embodiments herein.

In some embodiments, the bulk food product may comprise a plurality of meal portions, each meal portion comprising protein, fat, carbohydrates from a starch source, carbohydrate from a non-starch vegetable source, and fiber. In some embodiments, each meal portion may further comprise a phyto blend comprising an ingredient selected from mushroom powder, moringa leaf extract, ginger, turmeric, saffron, a natural supplement blend, digestive enzymes, probiotics (e.g. *Bacillus subtilis* or *B. coagulans*), fruits, vegetables, herbs, or a combination thereof.

The protein may be obtained from food sources known to be high in protein. Specifically, the protein source may be selected from lean meat, such as chicken without skin, beef, pork and fish. Alternatively, the protein source may be selected from a variety of beans to create a vegetarian-friendly bulk food product.

The carbohydrate from the non-starch vegetable source may be obtained from any vegetable source including, but not limited to, carrot, spinach and other non-starch vegetables.

The carbohydrate from the starch source may be obtained from any starch source including, but not limited to, potatoes, rice and yams (or sweet potato).

The phyto blend may include a selection of natural plant based foods, such as wheat grass, flax, wheat germ and other ingredients high in nutrition and fiber. The phyto blend may also include enzymes and probiotics that are conducive to health. In some embodiments, the phyto blend may comprise at least one of mushroom powder, moringa leaf extract, ginger, turmeric, saffron, a natural supplement blend, digestive enzymes, probiotics (e.g. *Bacillus subtilis* or *B. coagulans*), fruits, vegetables, and herbs. In some embodiments, the ginger is a ginger rhizome. In some embodiments, the turmeric is turmeric rhizome. In some embodiments, the phyto blend may comprise the ingredients set out in Table 1.

TABLE 1

| PHYTO BLEND | |
|---|---|
| Amount Per Serving | Dosage/day |
| Fruit, vegetable, cereal grass, herbal, and phytonutrient blend | 500 mg |
| Reishi (*Ganoderma lucidum*) mycelial biomass powder | 250 mg |
| Shiitake (*Lentinus edodes*) mycelial biomass powder | 250 mg |
| Moringa (*Moringa oleifera*) leaf extract (10:1 or TBD) | 500 mg |
| *Bacillus subtilis** | 50 mg |
| *Bacillus coagulans** | 133.33 mg |
| Saffron (*Crocus sativus*) stigma extract [standardized to 0.2% safranal] | 30 mg |
| Ginger (*Zingiber officinale*) rhizome powder | 200 mg |
| Turmeric (*Curcuma longa*) rhizome powder | 500 mg |

**B. subtilis* = 5 billion/cfu/day; *B. coagulans* = 2 billion/cfu/day

In some embodiments, the natural supplement blend may be selected from a fruit, vegetable, cereal grass, herbal, and phytonutrient blend, such as that sold under the tradename Spectra™ or Amazing Grass® Green Superfood®. The natural supplement may be in an amount of about 100 mg to about 1000 mg, about 200 mg to about 1000 mg, about 300 mg to about 1000 mg, about 400 mg to about 1000 mg, about 500 mg to about 1000 mg, about 100 mg to about 500 mg, about 200 mg to about 500 mg, about 300 mg to about 500 mg, about 400 mg to about 500 mg, or a value within any of these ranges. The natural supplement may be in an amount of about 100 mg, about 200 mg, about 300 mg, about 400 mg, about 500 mg, about 600 mg, about 700 mg, about 800 mg, about 900 mg, about 1000 mg, or a range of any two of these values.

In some embodiments, the mushroom powder may comprise any type of mushroom. In some embodiments, the mushroom powder may comprise reishi mushroom, shiitake mushrooms, or a combination thereof. In some embodiments, the mushroom powder may be in an amount of about 100 mg to about 1000 mg, about 200 mg to about 1000 mg, about 300 mg to about 1000 mg, about 400 mg to about 1000 mg, about 500 mg to about 1000 mg, about 100 mg to about 500 mg, about 200 mg to about 500 mg, about 300 mg to about 500 mg, about 400 mg to about 500 mg, or a value within any of these ranges. The mushroom powder may be in an amount of about 100 mg, about 200 mg, about 300 mg, about 400 mg, about 500 mg, about 600 mg, about 700 mg, about 800 mg, about 900 mg, about 1000 mg, or a range of any two of these values.

In some embodiments, the moringa leaf extract may have an extract ratio of about 20:1, about 15:1, about 10:1, about 6:1, about 5:1, about 4:1, or the like. In some embodiments, the extract ratio is about 10:1. In some embodiments, the mushroom powder may be in an amount of about 100 mg to about 1000 mg, about 200 mg to about 1000 mg, about 300 mg to about 1000 mg, about 400 mg to about 1000 mg, about 500 mg to about 1000 mg, about 100 mg to about 500 mg, about 200 mg to about 500 mg, about 300 mg to about 500 mg, about 400 mg to about 500 mg, or a value within any of these ranges. The moringa leaf extract may be in an amount of about 100 mg, about 200 mg, about 300 mg, about 400 mg, about 500 mg, about 600 mg, about 700 mg, about 800 mg, about 900 mg, about 1000 mg, or a range of any two of these values.

The saffron stigma extract may be derived with Crocus sativus. In some embodiments, the saffron stigma extract is in an amount of about 5 mg to about 60 mg, about 10 mg to about 60 mg, about 15 mg to about 60 mg, about 20 mg to about 60 mg, about 25 mg to about 60 mg, about 30 mg to about 60 mg, about 5 mg to about 45 mg, about 10 mg to about 45 mg, about 15 mg to about 45 mg, about 20 mg to about 45 mg, about 25 mg to about 45 mg, about 30 mg to about 45 mg, about 5 mg to about 30 mg, about 10 mg to about 30 mg, about 15 mg to about 30 mg, about 20 mg to about 30 mg, about 25 mg to about 30 mg, or a value in any of the ranges. In some embodiments, the saffron stigma extract is in an amount of about 5 mg, about 10 mg, about 15 mg, about 20 mg, about 25 mg, about 30 mg, about 45 mg, about 50 mg, about 55 mg, about 60 mg, or a range between any two of these values. In some embodiments, the saffron stigma extract comprises safranal in an amount of about 0.01% to about 0.3%, about 0.01% to about 0.2%, about 0.05% to about 0.3%, about 0.05% to about 0.2%, about 0.1% to about 0.2%, about 0.1% to about 0.3%, about 0.15% to about 0.2%, about 0.15% to about 0.3%, or a value within any of these ranges. In some embodiments, the saffron stigma extract comprises safranal in an amount of about 0.2%, about 0.1%, about 0.15%, about 0.01%, about 0.05%, or a range between any two of these values.

In some embodiments, the ginger rhizome comprises Zingiber officinale. In some embodiments, the ginger rhizome is in an amount of about 1 mg to about 100 mg, about 5 mg to about 100 mg, about 10 mg to about 100 mg, about 20 mg to about 100 mg, about 30 mg to about 100 mg, about 40 mg to about 100 mg, about 50 mg to about 100 mg, about 1 mg to about 75 mg, about 5 mg to about 75 mg, about 10 mg to about 75 mg, about 20 mg to about 75 mg, about 30 mg to about 75 mg, about 40 mg to about 75 mg, about 50 mg to about 75 mg, about 1 mg to about 50 mg, about 5 mg to about 50 mg, about 10 mg to about 50 mg, about 20 mg to about 50 mg, about 30 mg to about 50 mg, about 40 mg to about 50 mg, about 1 mg to about 45 mg, about 5 mg to about 45 mg, about 10 mg to about 45 mg, about 20 mg to about 45 mg, about 30 mg to about 45 mg, about 40 mg to about 45 mg, or a value within any of these ranges. In some embodiments, the ginger rhizome comprises gingerols in an amount of about 0.01% to about 10%, about 0.1% to about 10%, about 0.5% to about 10%, about 1% to about 10%, about 2% to about 10%, about 3% to about 10%, about 4% to about 10%, about 5% to about 10%, 0.01% to about 5%, about 0.1% to about 5%, about 0.5% to about 5%, about 1% to about 5%, about 2% to about 5%, about 3% to about 5%, about 4% to about 5%, at least about 5%, at least about 1%, or a value within any of these ranges. In some embodiments, the ginger rhizome comprises gingerols in an amount of about 0.01%, about 0.1%, about 0.5%, about 1%, about 2%, about 3%, about 4%, about 5%, about 10%, or a range of any two of these values.

In some embodiments, the turmeric rhizome may be in an amount of about 10 mg to about 500 mg, about 25 mg to about 500 mg, about 50 mg to about 500 mg, about 75 mg to about 500 mg, about 100 mg to about 500 mg, about 10 mg to about 250 mg, about 25 mg to about 250 mg, about 50 mg to about 250 mg, about 75 mg to about 250 mg, about 100 mg to about 250 mg, about 10 mg to about 100 mg, about 25 mg to about 100 mg, about 50 mg to about 100 mg, about 75 mg to about 100 mg, or a value within any of these ranges. In some embodiments, the turmeric rhizome may be in an amount of about 10 mg, about 25 mg, about 50 mg, about 75 mg, about 100 mg, about 200 mg, about 250 mg, about 300 mg, about 400 mg, about 500 mg, or a range of any two of these values.

In some embodiments, the probiotics is in an amount of about 1 mg to about 100 mg, about 5 mg to about 100 mg, about 10 mg to about 100 mg, about 20 mg to about 100 mg, about 30 mg to about 100 mg, about 40 mg to about 100 mg, about 50 mg to about 100 mg, about 1 mg to about 75 mg, about 5 mg to about 75 mg, about 10 mg to about 75 mg, about 20 mg to about 75 mg, about 30 mg to about 75 mg, about 40 mg to about 75 mg, about 50 mg to about 75 mg, about 1 mg to about 50 mg, about 5 mg to about 50 mg, about 10 mg to about 50 mg, about 20 mg to about 50 mg, about 30 mg to about 50 mg, about 40 mg to about 50 mg, or a value within any of these ranges. In some embodiments, the probiotics may comprise a Bacillus (e.g. B. subtilis or B. coagulans), a Lactobacillus (L. acidophilus, L plantarum, or L. reuteri), a Bifidobacterium (e.g. B. animalis, B. breve, B. lactis, B. longum, or B. infantis), a Streptococcus (S. salivarius K12 or S. Salivarius M18), combinations thereof, or any other probiotic. In some embodiments, the probiotic is in an amount of about 1 million cfu to about 10 million cfu, about 2 million cfu to about 10 million cfu, about 3 million cfu to about 10 million cfu, about 4 million cfu to about 10 million cfu, about 5 million cfu to about 10 million cfu, about 1 million cfu to about 8 million cfu, about 2 million cfu to about 8 million cfu, about 3 million cfu to about 8 million cfu, about 4 million cfu to about 8 million cfu, about 5 million cfu to about 8 million cfu, about 1 million cfu to about 5 million cfu, about 2 million cfu to about 5 million cfu, about 3 million cfu to about 5 million cfu, about 4 million cfu to about 5 million cfu, or a value in any of these ranges. In some embodiments, the probiotic is in an amount of about 1 million cfu, about 2 million cfu, about 3 million cfu, about 4 million cfu, about 5 million cfu, about 6 million cfu, about 7 million cfu, about 8 million cfu, about 9 million cfu, about 10 million cfu, or a range of any two of these values.

The units above for the phyto blend and the weight loss composition composition may be daily amounts that could be administered as one or more servings.

The natural preservative blend may include natural ingredients which preserve food and provide flavor such as sea salt, lemon, rosemary oil, garlic and other natural flavorings.

The ingredients may be selected to create a variety of different bulk food products suitable to different tastes e.g. suitable ingredients can be selected to produce a sweet food product, a savory food product, a vegetarian food product, etc. In some embodiments, the bulk food product may be in a form which may be diluted to create a stew or a soup (such as a jarred or otherwise packaged concentrate).

The size of a serving is preferably adequate to provide sufficient energy to support the caloric requirements of a subject for about 3 to 5 hours depending on the subject's energy expenditure or objective.

While a meal portion of the bulk food product is flexible, a baseline serving for each meal portion has been established as between about 400 g to about 525 g of the bulk food product. This is approximately equal to 400 to 525 calories. In some embodiments, the baseline serving is about 450 g of the food product which provides approximately 450 calories.

In some embodiments, each meal portion includes about 26 g to about 40 g of protein, about 7 g to about 16 g of fat, about 15 g to about 20 g of carbohydrate from a starch source, about 20 g to about 30 g of carbohydrate from a vegetable source or non-starch source (such as beans and legumes), and about 11 g to about 21 g of fiber. In some embodiments, the meal portion further includes about 1 g to about 10 g of a phyto blend, about 1 g to about 3 g of a natural preservative blend, or a combination thereof. In some embodiments, each meal portion includes protein in an amount of about 5% to about 9%, fat in an amount of about 1% to about 4%, carbohydrate from a starch source in an amount of about 3% to about 5%, carbohydrate from a vegetable or non-starch source in an amount of about 4% to about 7%, and fiber in an amount of about 2% to about 5%. In some embodiments, each meal portion may further include a phyto blend in an amount of about 0.2% to about 2.5%, a natural preservative blend in an amount of about 0.2% to about 0.8%, or a combination thereof.

In some embodiments, the bulk food product may include at least two meal portions, at least three meal portions, at least five meal portions, at least 7 meal portions, about 2 to about 24 meal portions, about 3 to about 24 meal portions, about 5 to about 24 meal portions, about 7 to about 24 meal portions, about 8 to about 24 meal portions, about 14 to about 24 meal portions, about 21 to about 24 meal portions, about 2 to about 21 meal portions, about 3 to about 21 meal portions, about 5 to about 21 meal portions, about 7 to about 21 meal portions, about 8 to about 21 meal portions, about 14 to about 21 meal portions, or a value within these ranges. In some embodiments, The bulk food product may be a mixture packaged with at least one scoop or cup, of a defined size, to measure out a meal portion or fractions thereof. For example, a measuring cup could be provide which measures out one half of the recommended meal portion of the bulk food product. After packaging, the bulk food product may be snap frozen or refrigerated.

The food product may be used to implement any type of balanced diet and can be used for weight loss, weight maintenance or weight gain purposes, or as a snack or meal substitute. For example, the bulk food product may be used to implement a calorie restricted diet for weight loss, by reducing the amount of the food product which is consumed per meal. The bulk food product may also be used to implement the weight management plan of embodiments herein. In some embodiments, the food product may be used, for example by adolescents or athletes, to gain weight healthily by increasing the size of the portion of the food product, i.e. the amount, consumed per meal. Additional portions may also be consumed as snacks between meals. A side dish, such as an egg or a salad, may be added as required by a subject. For example, an athlete/bodybuilder may wish to add an extra protein source in the form of an egg etc.

Exemplary benefits of the bulk food product include convenience, ease of use, and improved adherence to a nutrition and exercise program, such as the weight loss plan of embodiments herein. The bulk food product comprises a plurality of complete balanced meal portions. Each meal portion is associated with a food value that is easy to keep track of and correlate with the daily base food allowance for the subject in the weight management plan of embodiments herein. Additionally, when consuming a meal portion of the bulk food product, the subject is assured that the meal is balanced and contains ingredients selected from all varieties of foods, categorized in terms of their fiber and essential nutrient content, ensuring that the essential nutrients are present in a ratio which is optimal for stabilizing insulin resistance.

The bulk food product and the accompanying weight management plan further affords the subject freedom to choose when to eat all or a part of his/her daily base food allowance. Additionally, because the responsibility or discretion placed on the subject to select ingredients is removed, the bulk food product has a substantial psychological benefit in that the consumer is relieved of the flexibility of choice and, when eating a complete meal product is inherently assured of consuming the appropriate number of food units, containing fiber and the three essential nutrients in the correct combinations and proportions to follow the weight management plan of embodiments herein. Additionally, exemplary benefits of the weight loss composition of embodiments herein, as mentioned above, are to normalize insulin levels, control glucose and fat storage, balance hormones, and reduce insulin resistance as well as kickstart the metabolism in the subject to help them achieve their ideal weight.

Methods

Some embodiments herein are directed to a method of treating or preventing obesity in a subject comprising administering to the subject the weight loss composition of embodiments herein. In some embodiments, the subject concurrently follows a weight management plan of embodiments herein. In some embodiments, the subject uses the bulk food product of embodiments herein to at least partly follow the weight management plan.

Some embodiments herein are directed to a method for promoting weight loss in a subject, the method comprising administering to the subject the weight loss composition of embodiments herein. In some embodiments, the subject concurrently follows a weight management plan of embodiments herein. In some embodiments, the subject uses the bulk food product of embodiments herein to at least partly follow the weight management plan.

Some embodiments herein are directed to a method of improving insulin resistance in a subject, the method comprising administering to the subject the weight loss composition of embodiments herein. In some embodiments, the subject concurrently follows a weight management plan of embodiments herein. In some embodiments, the subject uses the bulk food product of embodiments herein to at least partly follow the weight management plan.

This invention and embodiments illustrating the method and materials used may be further understood by reference to the following non-limiting examples.

Example 1

Effect of the GOLO Diet (Weight Management Plan) and GOLO Release Supplement (Weight Loss Composition) on Weight, Glycemic Control and Indicators of Insulin Sensitivity in Overweight and Obese Patients with Type 2 Diabetes Summary: 26 subjects with type 2 diabetes mellitus were recruited in an open-label study of the GOLO Diet with Release supplement at a single clinical site. 15 subjects completed the study over the 13-week treatment period. Overall weight loss averaged 7.9 lbs (−3.8%) and BMI levels dropped by 1.3 (−3.7%). Markers of glycemic control improved with Hemoglobin A1C (−9.2%) and fasting blood glucose (−17.9%) decreasing while markers of insulin resistance including insulin levels (−18.7%) and HOMA-IR (−36.6%) showed substantial improvement. Favorable improvement was also noted in other laboratory results and clinical measures including cholesterol levels and inflammation.

Introduction: Excess body weight from overeating, poor nutrition and lack of exercise is highly correlated with health status. Clinical weight loss in overweight and obese people is associated with improvements in clinical markers of health, including key measures of blood sugar and blood lipids used to determine a person's health status Populations who are overweight and obese include people who exhibit a wide range of blood sugar levels, ranging from healthy to pre-diabetic to type 2 diabetes. Overweight and obese people on this spectrum often have difficulty obtaining meaningful or sustained weight loss. Body weight is also a leading indicator of high blood sugar levels. It is well established that people who are healthy, pre-diabetic or diabetic who lose weight and exercise tend to lower their measures of blood sugar and blood lipids, and are more likely to improve their health status (1).

GOLO has created a weight management program that includes a supplement (weight loss composition) known as Release and (GWMP) and is designed to help people who are overweight or obese get the proper balance of macro and micro nutrients from conventional foods, in the proper portions and combinations to help keep insulin steady for weight loss, and help them to transition to a healthier lifestyle. The GWMP includes a point-based system from the four macronutrient food groups that is based on the individual's activity level and body mass. Additionally, the program includes common-sense instructions, motivation and tips supporting compliance and recommends a minimum of 15 minutes of exercise per day. The Release dietary supplement contains 7 plant based ingredients and 3 minerals including zinc and chromium, essential nutrients that support regulation of blood sugar.

In case studies from clinician and wellness program use, GWMP has shown the ability to reduce body weight in both healthy and diabetic people who are overweight or obese. Secondary endpoints including measures of blood sugar have been observed to decrease as a result of the GWMP program (2).

While the GWMP has been developed and used in private clinical practice in both healthy overweight and type 2 diabetic people, more systematic research is needed to determine to what extent it is able to support healthy weight loss. This open-label pilot study is intended to observe the effects of the program in a representative group of subjects with stable type 2 diabetes at one outpatient medical practice.

Study design: This observational study evaluating the effect of the GOLO Weight Management Program (GWMP) on weight and metabolic syndrome indicators in overweight or obese subjects with stable type 2 diabetes mellitus was conducted at one clinical site in the United States. The study consisted of 4 visits over approximately 13 weeks.

At visit 1, study eligibility was determined and subjects were given the commercially available GOLO Weight Management Program and instructed on the program's diet and exercise guidelines. Subjects were given the Release Supplement and instructed to take one capsule three times a day with meals. Laboratory and body measurements were obtained. Visit 2 was a telephone call to subjects to assess tolerability of the program. At approximately week 4, subjects returned for Visit 3 for a compliance and tolerability assessment and body measurements. The final visit 4 occurred at approximately week 13 and included body measurements, laboratory analysis and compliance and tolerability assessment.

Body measurements included fasting weight, height, waist and hip circumference, and resting blood pressure and pulse were taken at each visit. A Tanita scale was used to calculate BMI, body fat and visceral fat. Laboratory evaluation included hemoglobin A1C, fasting insulin, fasting blood glucose, lipid panel, metabolic panel including liver testing, hsCRP, CBC, sex hormones, and PSA in men. Homeostatic model assessment of insulin resistance HOMA-IR was calculated using the formula (Fasting Blood Glucose) (Fasting Insulin)/22.5(3). Stress and Anxiety were measured at visit 1 and visit 4 using a standardized Stress Questionnaire.

Subjects: 26 subjects consented to participate in the study. One subject screen failed for a BMI outside of inclusion criteria. 10 subjects withdrew or were removed from the study for the following reasons: 5 lost to follow-up/voluntarily withdrew, 3 adverse events and 2 poor study compliance. 15 subjects completed the study and attended all 4 visits.

Results: 5 Males and 10 Females completed the study. The average age of males was 57.8 and females 58.5. The average starting weight was 206.3 pounds and BMI 34.3 which is considered obese. Average hemoglobin A1c (7.5) and fasting blood glucose (153.7) were elevated at baseline indicating poorly controlled type 2 DM. Initial resting blood pressure (124.1/75.5) and LDL cholesterol (100.5) were already at or near goal levels in this group of diabetic subjects, primarily due to pre-study treatment with blood pressure and cholesterol medications.

Changes from baseline visit 1 to visit 4 in weight, BMI, body analysis and body measurements are listed in Table 2. Overall weight loss averaged 7.9 lbs (−3.8%) and BMI levels dropped by 1.3 (−3.7%). Loss of Fat Mass (−7.2%) were more pronounced in this overweight/obese population. Waist measurements (−6.1%) improved more than hip measurements (−3.5%) resulting in a favorable change in waist/hip ratio (−6.1%). Changes in resting blood pressure and pulse were minimal as the majority of subjects were treated with blood pressure medication as is standard care in diabetic patients. Changes in the Stress/Anxiety survey were substantial (−49.0%).

TABLE 2

CHANGES IN WEIGHT AND BODY MEASUREMENTS

|  | Visit 1 (Week 1) | Visit 4 (Week 13) | Change |
| --- | --- | --- | --- |
| Weight (lbs.) | 206.3 | 198.4 | −7.9 (−3.8%) |
| BMI | 34.3 | 33 | −1.3 (−3.7%) |
| Fat Mass (lbs.) | 77.7 | 72.1 | −5.6 (−7.2%) |
| Visceral Fat Rating | 13.8 | 12.8 | −1.0 (−7.2%) |
| Waist (cm) | 113.6 | 106.7 | −6.9 (−6.1%) |
| Hips (cm) | 115 | 111 | −4.0 (−3.5%) |
| Waist/Hip Ratio | 1.77 | 1.66 | −0.1 (−6.1%) |
| Stress/Anxiety Score | 10.5 | 5.3 | −5.1 (−49.0%) |

Changes from baseline visit 1 to visit 4 in markers of glycemic control and insulin sensitivity are listed in Table 3. Levels of Hemoglobin A1C (−9.2%), a measurement of DM control over a 3-month period improved while fasting blood glucose improvement was even more pronounced (−17.9%). Markers of insulin resistance, an important cause of type 2 DM and other diseases, decreased greatly with insulin levels falling (−18.7%) and HOMA-IR, a standard calculation of insulin resistance, dropping even more extensively (−36.6%).

TABLE 3

CHANGES IN MARKERS OF GLYCEMIC CONTROL AND INSULIN RESISTANCE

|  | Visit 1 (Week 1) | Visit 4 (Week 13) | Change |
| --- | --- | --- | --- |
| Hemoglobin A1C | 7.5 | 6.8 | −0.7 (−9.2%) |
| Insulin Level (uIU/ml) | 15.8 | 12.8 | −3.0 (−18.7%) |
| Fasting Glucose (mg/dl) | 153.7 | 126.3 | −27.5 (−17.9%) |
| HOMA-IR | 6.5 | 4.1 | −2.4 (−36.6%) |

Changes from baseline visit 1 to visit 4 in total and LDL cholesterol levels were minimal but favorable in this group of subjects that generally were already being treated with statin medications. (Table 4) Improvements in HDL levels were more substantial (3.4%) as were improvements in triglyceride levels (−12.1%). Levels of hsCRP a marker of general inflammation and associated with cardiovascular risk were reduced (−2.8%).

TABLE 4

CHANGES IN LIPID PANEL

|  | Visit 1 (Week 1) | Visit 4 (Week 13) | Change |
| --- | --- | --- | --- |
| Total Cholesterol (mg/dl) | 179.1 | 177.2 | −1.9 (−1.0%) |
| LDL Cholesterol (mg/dl) | 100.5 | 99.8 | −0.7 (−0.7%) |
| HDL Cholesterol (mg/dl) | 43.7 | 45.2 | 1.5 (3.4%) |
| Triglycerides | 183.1 | 161.0 | −22.1 (−12.1%) |
| hsCRP | 5.5 | 5.3 | −0.2 (−2.8%) |

Discussion: Among the 15 subjects completing this study, weight loss was demonstrated and averaged 7.9 pounds over 13 weeks. This weight loss is impressive because treatments for type 2 DM often are associated with weight gain. One explanation for this usual weight gain is that as blood sugar control is improved with intervention, less glucose is generally lost through renal oversaturation (glycosuria), retaining these calories, and weight gain is often seen initially with diabetic treatments. Generally, any weight loss achieved in the first 3 months of diabetes treatment is considered important. In addition, the preferential loss of fat mass as demonstrated in this study is particularly desirable in treating type 2 DM.

Improvements in glycemic control and insulin resistance were the most impressive results of the study. Hemoglobin A1C and fasting blood glucose over 13 weeks compares favorably with traditional oral anti-diabetic treatments like metformin or pioglitazone. While the initial average A1C at baseline (7.5) indicated poor diabetic control, the average A1C level at V4 (6.8) met the goal A1C level recommended for diabetic patients (less than 7.0). Changes in fasting insulin level and HOMA-IR actually exceeded that seen with these prescribed medications. The large improvements in insulin resistance demonstrated by the GWMP system with the Release supplement suggest a beneficial role in other disease states including the Metabolic Syndrome.

Favorable changes to other laboratory tests were observed from baseline visit 1 to visit 4 and are listed in Table 5. Improvement in liver transaminase enzymes (AST and ALT) are often seen with weight loss and most likely reflect decreased inflammation from fatty liver. Changes in sex hormones are also seen following weight loss and represent decrease peripheral fat conversion of hormone pre-cursers and suggest a benefit in patients with Polycystic Ovary Disease (PCOS). No other significant changes in metabolic panel values, PSA or other safety variables were observed. Three subjects terminated from the study due to gastrointestinal adverse events including loose bowel movements or abdominal cramps. No serious adverse events were identified.

TABLE 5

CHANGES IN LIVER TRANSAMINASES AND SEX HORMONES

|  | Visit 1 (Week 1) | Visit 4 (Week 13) | Change |
| --- | --- | --- | --- |
| AST (mg/dl) | 28.2 | 24.7 | −3.5 (−12.3%) |
| ALT (mg/dl) | 34.4 | 29.9 | −4.5 (−13.0%) |
| Progesterone (women) | 1.1 | .3 | −0.8 (−76.9%) |
| Estradiol (women) | 34.4 | 24.8 | −9.6 (−27.9%) |

The Stress/Anxiety questionnaire was a 20-question self-administered written test that served as a general marker of psychological health. Although the study was not statistically powered for this endpoint, the change in average score on this questionnaire was impressive (−49%) and suggest the opportunity for further study.

The study was limited by selection of subjects at only one clinical site. In addition, the study was open-label and lacks the rigor of a double-blinded placebo-controlled study. In addition, poor subject compliance with the GWMP diet and exercise component may also have influenced the results of the study. Although compliance with the Release supplement as obtained by pill counts (95 percent overall compliance by pill count) was excellent, compliance with diet and exercise recommendations was variable and more difficult to quantify. The relatively high drop-out rate ($^{10}/_{25}$—40%) of the subjects consented for the study reflect this difficulty in obtaining compliance with the program. Frustration with previous diet plans and unrealistic expectations about life-style change likely contributed to drop outs. In addition, enrolling a population with type 2 diabetes that likely has failed other attempts at diet, exercise and medical therapy presented challenges to compliance.

In summary, the GOLO Weight Management Program with the Release supplement demonstrated weight loss and improvement in glycemic control comparable to standard prescription anti-diabetic medications in this small, single center study. Improvements in markers of insulin resistance were impressive and exceeded those seen by existing anti-diabetic medications including the Gold Standard for treatment of insulin resistance pioglitazone. Further studies will be needed to evaluate the role of the GOLO Weight Management Program with the Release supplement in diabetic and non-diabetic populations.

Example 2

Efficacy of a Diet Program on Body Weight in Overweight and Obese South Africans

Background

Over the course of several years the Medical Nutritional Institute (MNI) based in Johannesburg South Africa developed a weight loss program to help combat obesity and weight related conditions. The program included a lifestyle change plan, meal plan and dietary supplement labeled as Antagolin.

Five studies were conducted in South Africa, in Cape Town and Johannesburg during 2009-2014 (Table 6). The studies are referred to by the names SANLAM, ABSA, SAMANCOR, X-STRATA, and LIGHTHOUSE.

NaturPro Scientific LLC reviewed all study data provided and evaluated the apparent integrity and completeness of the data, and conducted statistical analysis, and wrote the reports. Data for each study was analyzed independently and then in a pooled analysis that combined study data of the same duration (12 or 25-27 weeks). All data from subjects completing the study were analyzed based on changes in endpoints from baseline using means, standard deviation and single-factor ANOVA (Microsoft Excel).

Methods

Participants for these studies were recruited through their employer as part of a wellness initiative. With the exception of ABSA which was 12 weeks only, all studies were designed as 12-weeks in duration, with the option given to subjects to continue the study for an additional 13 weeks.

The study subjects participated in one of two treatment groups: the Complete Program, or the Program without the dietary supplement, which was named the "Control Program".

TABLE 6

SUMMARY OF NUMBER OF SUBJECTS AND LENGTH OF STUDIES.
South Africa Study Summary

| Study | Length Weeks | Subjects (N) | Treatment | Year |
|---|---|---|---|---|
| SANLAM (12 wks) | 12 | 17 | Complete Program | 2009 |
|  | 12 | 4 | Control-Program Only |  |
| SANLAM (Ext 25 wks) | 25 | 17 | Complete Program |  |
|  | 25 | 4 | Control-Program Only |  |
| SANLAM (Ext 61 wks) | 61 | (subset of 8 obese) | Complete Program |  |
| SANLAM (Ext 102 wks) | 102 | (subset of 6 obese) | Complete Program |  |
| ABSA | 12 | 13 | Complete Program | 2010 |
|  | 12 | 5 | Control-Program Only |  |
| SAMANCOR | 12 | 14 | Complete Program | 2011 |
|  | 12 | 6 | Control-Program Only |  |
| SAMANCOR (Ext 27 wks) | 27 | (subset of 10) | Complete Program |  |
| XSTRATA | 12 | 22 | Control-Program Only | 2012 |
|  | 29 | 22 | Control-Program Only |  |
| LIGHTHOUSE | 12 | 10 | Complete Program | 2014 |
|  | 16 | 10 | Complete Program |  |
| Pooled 12 Week | 12 | 54 | Complete Program |  |
| Results | 12 | 37 | Control-Program Only |  |
| Pooled 25 Week | 25-27 | 27 | Complete Program |  |
| Results | 25-29 | 26 | Control-Program Only |  |

Intervention

The Program portion of the system included tools for achieving a healthy lifestyle which included an eating plan based on portion control and caloric restriction, behavior modification guidance in the form of booklets that included a self-assessment and an exercise guide promoting strength and circuit training exercise to support cardiovascular and muscle maintenance and development.

The supplement contained a blend of plant-derived ingredients and minerals consisting of banaba leaf, barberry bark extract, inositol, and chromium. Recommended dosage was 2 capsules twice a day.

The Program including the supplement was termed the "Complete Program", and the Program without the supplement was named the "Control Program".

Inclusion and Exclusion Criteria

Adults older than 20 years old, with a body mass index>25 $kg/m^2$ were included in all studies. Subjects were required to be healthy, pre-diabetic or diabetic people measured as overweight or obese. Excluded were pregnant or lactating subjects, and individuals with known allergies to the dietary supplement or any of its ingredients, determined by questionnaire. Subjects were instructed to continue to take all medications that they were prescribed before entering the study. Any subsequent changes in medication were made under supervision of the subjects' personal physicians.

Study Endpoints

In all studies, food and exercise logs were recorded by subjects daily, and clinical and anthropometric measurements such as vital signs and body weight were measured by full time staff members of the company conducting the trial. Each had a recognized medical qualification, including registered nurses, a dietician, a biokineticist and a pharmacist.

Compliance and Follow-Up

Compliance was based on level of adherence to diet, supplementation and exercise recommendations as well as appearance for study visits. A minimum average compliance of 50% per subject was required for inclusion in the data analysis. After 26 weeks, obese subjects were invited to continue on the program for an additional 26 weeks.

Ethical Requirements

For all studies conducted, informed consent was given by all subjects. Study subjects were not compensated for participation.

Results

Overall, 54 subjects completed 12 weeks on the Complete Program, and 27 subjects continued for 25-27 weeks (See Table 6). 37 subjects on the control program completed 12 weeks, and 26 subjects on the control program completed 25-29 weeks. Of eight dropouts, none were due to study- or treatment-related issues. Table 18 below provides the reasons for all dropouts.

In the SANLAM study, an average of 32.1 and 53.4 pounds were lost after 12 and 26 weeks, respectively, in those subjects using the Complete Program (Table 8).

TABLE 8

AVERAGE BODY WEIGHT FOR SUBJECTS IN THE SANLAM STUDY ON THE COMPLETE PROGRAM.

| SANLAM (n = 17) | Baseline | 12 weeks | 26 weeks |
|---|---|---|---|
| Weight (lb) | 270.9 | 238.8 | 217.4 |
| p-value | | 0.08 | 0.0041 |

A subset of 8 obese subjects in SANLAM who began the study weighing more than 240 pounds and who completed the initial 25 weeks continued the Complete Program for an additional 36 weeks (61 weeks total) experienced an average weight loss of 62 pounds (Table 7). The difference from baseline trended to significance (p<0.059). Six of these subjects continued for an additional 41 weeks (102 weeks total), and this group experienced an average weight loss of 83 pounds (p=0.03).

A trend for significant reduction in body weight (lb) (p=0.059) was observed for 8 obese subjects in SANLAM (arbitrarily coded A-H) who continued on the trial for more than one year (61 weeks).

TABLE 9

SANLAM RESULTS IN OBESE SUBJECTS USING THE COMPLETE PROGRAM.

| Subject | Baseline | 1 year | Change (lbs) |
|---|---|---|---|
| A | 426 | 354 | −72 |
| B | 252 | 209 | −43 |

TABLE 7

SOUTH AFRICA STUDY SUMMARY AVERAGE STUDY RESULTS IN INDIVIDUAL STUDIES AND IN POOLED RESULTS--SANLAM STUDY

| Study | Length Weeks | Subjects (N) | Treatment | Weight Loss (lb) | Weekly Loss (lb) | Waist Loss (inches) |
|---|---|---|---|---|---|---|
| SANLAM (12 wks) | 12 | 17 | Complete Program | 32.1 | 2.7 | * |
| | 12 | 4 | Control-Program Only | 8.9 | 0.7 | * |
| SANLAM (Ext 25 wks) | 25 | 17 | Complete Program | 53.4 | 2.1 | 6.8 |
| | 25 | 4 | Control-Program Only | 9.5 | 0.4 | 6.3 |
| SANLAM (Ext 61 wks) | 61 | (subset of 8 obese) | Complete Program | 62.0 | 1.0 | 10.4 |
| SANLAM (Ext 102 wks) | 102 | (subset of 6 obese) | Complete Program | 83.8 | 0.8 | 12.1 |
| ABSA | 12 | 13 | Complete Program | 16.7 | 1.4 | 3.8 |
| | 12 | 5 | Control-Program Only | 7.7 | 0.6 | 0.7 |
| SAMANCOR | 12 | 14 | Complete Program | 20.5 | 1.7 | 2.2 |
| | 12 | 6 | Control-Program Only | 5.5 | 0.5 | 2.2 |
| SAMANCOR (Ext 27 wks) | 27 | (subset of 10) | Complete Program | 32.6 | 1.2 | 4.7 |
| X-STRATA | 12 | 22 | Control-Program Only | 6.7 | 0.6 | * |
| | 29 | 22 | Control-Program Only | 10.4 | 0.4 | 2.7 |
| LIGHTHOUSE | 12 | 10 | Complete Program | 9.0 | 0.8 | * |
| | 16 | 10 | Complete Program | 21.6 | 1.4 | 5.0 |
| Pooled 12 Week Results | 12 | 54 | Complete Program | 24.0 | 2.0 | * |
| | 12 | 37 | Control-Program Only | 8.1 | 0.7 | * |
| Pooled 25 Week Results | 25-27 | 27 | Complete Program | 44.9 | 1.7 | 6.8 |
| | 25-29 | 26 | Control-Program Only | 8.9 | 0.3 | 3.4 |

* not measured

TABLE 9-continued

SANLAM RESULTS IN OBESE SUBJECTS USING THE COMPLETE PROGRAM.

| Subject | Baseline | 1 year | Change (lbs) |
|---|---|---|---|
| C | 242 | 176 | −65 |
| D | 315 | 252 | −63 |
| E | 255 | 176 | −79 |
| F | 321 | 255 | −67 |
| G | 251 | 224 | −27 |
| H | 267 | 184 | −83 |
| AVG | 291 | 229 | −62 |

ABSA Study

Thirteen subjects on the Complete Program entered and completed the 12-week ABSA study. An average reduction in weight of 16.7 pounds was observed, although this result was not significant (p=0.46).

TABLE 10

AVERAGE BODY WEIGHT FROM ABSA IN SUBJECTS ON THE COMPLETE PROGRAM.

| ABSA (n = 13) | Baseline | 12 weeks |
|---|---|---|
| Weight (lb) | 229.0 | 212.3 |
| p-value | | 0.46 |

A subset of four subjects in the ABSA study on the Complete Program continued for 43 weeks. An average weight loss of 36.6 lb was observed in these subjects, and the result was significant despite the small sample size (p=0.05).

TABLE 11

AVERAGE BODY WEIGHT FROM ABSA FOR SUBJECTS CONTINUING ON THE STUDY FOR 43 WEEKS.

| ABSA (n = 4) | Baseline | 43 weeks |
|---|---|---|
| Weight (lb) | 186.1 | 149.5 |
| p-value | | 0.05 |

SAMANCOR Study

In the SAMANCOR study, 14 subjects using the Complete Program lost an average of 20.5 pounds, a result that was not significant due to the small sample size.

TABLE 12

AVERAGE BODY WEIGHT FROM SAMANCOR IN SUBJECTS ON THE COMPLETE PROGRAM.

| SAMANCOR (n = 14) | Baseline | 12 weeks |
|---|---|---|
| Weight (lb) | 239.4 | 218.9 |
| p-value | | 0.20 |

A subset of ten subjects using the Complete Program continued for 27 weeks in the SAMANCOR study, resulting in an average weight loss of 32.6 pounds, a significant result (p=0.001).

TABLE 13

AVERAGE BODY WEIGHT FROM SAMANCOR FOR SUBJECTS USING THE COMPLETE PROGRAM.

| SAMANCOR (n = 10) | Baseline | 27 weeks |
|---|---|---|
| Weight (lb) | 229.7 | 197.1 |
| p-value | | 0.001 |

Lighthouse Study

In the LIGHTHOUSE study, an average of 19.9 pounds were lost over 12 weeks, a result which was not significant (p=0.38).

TABLE 14

AVERAGE BODY WEIGHT FROM LIGHTHOUSE FOR SUBJECTS USING THE COMPLETE PROGRAM.

| LIGHTHOUSE (n = 10) | Baseline | 12 weeks |
|---|---|---|
| Weight (lb) | 223.8 | 203.9 |
| p-value | | 0.38 |

Pooled Results

A pooled analysis was conducted on studies with the same durations and study design in order to understand overall population effects. Pooled subjects completing 12 weeks on the Complete Program lost an average of 24.0 pounds, an effect which was significant from baseline (p=0.02). Subjects completing 25 weeks on the Complete Program lost an average of 44.9 pounds, which was also significant (p=0.0004).

TABLE 15

POOLED RESULTS OF AVERAGE BODY WEIGHT FOR SUBJECTS COMPLETING 12- AND 25-WEEK STUDIES.

| Study | Subjects (N) | Treatment | Length Weeks | Weight Loss (lb) | Weekly Loss (lb) | Waist Loss (inches) |
|---|---|---|---|---|---|---|
| Pooled | 54 | Complete GOLO Program | 12 | 24.0 | 2.0 | * |
| Pooled | 37 | Control-Program Only | 12 | 8.1 | 0.7 | * |
| Pooled | 27 | Complete GOLO Program | 25-27 | 44.9 | 1.7 | 6.8 |
| Pooled | 26 | Control-Program Only | 25-29 | 8.9 | 0.3 | 3.4 |

(* not measured).

The changes in body weight for control subjects pooled across the 12- and 25-week studies were similar to those previously published on other widely available diet programs. Although subjects in the control group lost an average of 8.1 and 8.9 pounds over 12 and 25 weeks, respectively, the effect was not significant (p>0.05).

Below, individual pooled 12-week data is shown.

TABLE 16

INDIVIDUAL RESULTS FOR AVERAGE BODY WEIGHT FOR SUBJECTS ON THE COMPLETE GOLO PROGRAM, POOLED FOR SUBJECTS COMPLETING 12 WEEKS.
Complete Program
Pooled 12-weeks

| Weight (lb) Baseline | 12 weeks |
|---|---|
| 255.3 | 211.2 |
| 245.6 | 195.8 |
| 267.2 | 224.2 |
| 252.0 | 218.5 |
| 321.2 | 280.2 |
| 201.1 | 173.9 |
| 425.9 | 369.3 |
| 270.3 | 243.2 |
| 241.6 | 218.9 |
| 245.1 | 219.8 |
| 240.5 | 222.2 |
| 360.9 | 282.4 |
| 251.3 | 232.8 |
| 315.3 | 284.8 |
| 239.9 | 221.3 |
| 208.3 | 176.4 |
| 263.0 | 239.4 |
| 203.0 | 186.5 |
| 240.1 | 210.5 |
| 214.1 | 197.2 |
| 242.5 | 220.3 |
| 253.1 | 218.7 |
| 199.5 | 191.8 |
| 255.3 | 237.9 |
| 254.9 | 229.7 |
| 227.7 | 204.4 |
| 207.0 | 181.0 |
| 197.1 | 179.7 |
| 249.1 | 227.5 |
| 368.2 | 339.5 |
| 240.3 | 238.3 |
| 249.1 | 228.6 |
| 205.8 | 184.3 |
| 295.9 | 263.0 |
| 219.6 | 203.5 |
| 175.0 | 154.2 |
| 228.0 | 208.6 |
| 303.8 | 294.3 |
| 165.8 | 147.3 |
| 233.7 | 210.1 |
| 160.2 | 145.1 |
| 212.1 | 189.2 |
| 173.1 | 150.4 |
| 177.0 | 158.3 |
| 257.3 | 244.5 |
| 200.6 | 189.8 |
| 297.6 | 282.2 |
| 197.1 | 183.0 |
| 140.4 | 130.3 |
| 297.4 | 292.3 |
| 280.9 | 245.8 |
| 181.9 | 153.4 |
| 249.8 | 230.6 |
| 311.3 | 309.5 |

TABLE 16-continued

INDIVIDUAL RESULTS FOR AVERAGE BODY WEIGHT FOR SUBJECTS ON THE COMPLETE GOLO PROGRAM, POOLED FOR SUBJECTS COMPLETING 12 WEEKS.
Complete Program
Pooled 12-weeks

| Weight (lb) Baseline | 12 weeks |
|---|---|
| 243.9 | 219.9 |
|  | Average |

Below, individual pooled 25-week data is shown.

TABLE 17

INDIVIDUAL RESULTS FOR AVERAGE BODY WEIGHT FOR SUBJECTS ON THE COMPLETE PROGRAM, POOLED FOR SUBJECTS COMPLETING 25 WEEKS.
Complete Program
Pooled 25-weeks

| Weight (lb) Baseline | 25 weeks |
|---|---|
| 203.0 | 188.3 |
| 227.7 | 197.1 |
| 240.1 | 196.1 |
| 214.1 | 186.3 |
| 253.1 | 207.2 |
| 242.5 | 202.8 |
| 199.5 | 184.1 |
| 255.3 | 228.0 |
| 254.9 | 222.7 |
| 207.0 | 179.7 |
| 360.9 | 229.5 |
| 255.3 | 178.8 |
| 245.6 | 172.6 |
| 267.2 | 189.8 |
| 252.0 | 200.2 |
| 321.2 | 255.5 |
| 201.1 | 160.3 |
| 425.9 | 341.9 |
| 270.3 | 224.9 |
| 239.9 | 201.1 |
| 241.6 | 205.9 |
| 251.3 | 216.0 |
| 208.3 | 181.7 |
| 315.3 | 275.1 |
| 245.1 | 216.0 |
| 240.5 | 212.5 |
| 263.0 | 235.0 |
| 255.6 | 210.7 |
|  | Average |

TABLE 18

WEIGHTS FOR SUBJECTS WITHDRAWING FROM THE STUDIES, AND REASON FOR WITHDRAWAL.

| Study | Duration (weeks) | Weight (lb) Baseline | End | Reason cited |
|---|---|---|---|---|
| SAN LAM | 14 | 259.9 | 257.5 | became pregnant |
| ABSA | 4 | 151.5 | 149.5 | work stress; failed to attend visits |
| ABSA | 8 | 179.7 | 172.4 | work stress; failed to attend visits |
| SAMANCOR | 8 | 210.1 | 203.3 | alcoholism |
| SAMANCOR | 4 | 419.8 | 399.3 | Work stress |
| X-STRATA | 0 | 305.1 | NA | failed to attend visits |
| X-STRATA | 4 | 219.1 | 207.5 | lost interest |
| X-STRATA | 8 | 331.8 | 289.0 | employment change |

Example 3

Efficacy of a Diet Program on Body Weight in Overweight Americans

Introduction

The NIH reports that 68.8% of adults in the USA are considered to be overweight or obese (35.7% obese and 6.3% have extreme obesity). It is generally accepted that being overweight increases risk factors for chronic disease. According to the Centers for Disease Control, 29.1 million Americans live with type 2 diabetes and 86 million with pre-diabetes. According to the U.S. National Institutes of Health, including the National Institute of Diabetes and Digestive and Kidney Diseases (NIDDK), high body weight and inadequate physical activity are two primary causes of insulin resistance and pre-diabetes. For many overweight people, changing dietary habits is key to maintaining a healthy body weight.

This report summarizes a pilot study performed in the USA to evaluate the safety and efficacy of a weight loss system originally developed and tested in South Africa by physicians at the Medical Nutritional Institute (MNI) in Johannesburg, South Africa, to provide a more effective weight loss solution.

BACKGROUND

MNI was started in 2002 to focus on weight management and healthcare training services. MNI developed the weight loss system to address previous limitations of corporate wellness programs to deliver sustainable weight loss and measurable health benefits. Conrad Smith M.D. and Mariaan Du Plessis (registered pharmacist) developed an approach to improve insulin management during weight loss programs. MNI developed a 3-tiered solution centered on insulin management in conjunction with caloric control and intervention with a plant and mineral based dietary supplement, containing ingredients researched to address insulin performance. MNI implemented two studies within corporate wellness programs in 2009 and 2010 and an additional three studies from 2011 through 2014.

In 2010, MNI partnered with GOLO, LLC in the USA (Newark, Delaware), and GOLO implemented a pilot study in 2011 to understand whether the initial results in South Africa could be replicated in a separate population of subjects.

Methods

A 26-week, open-label pilot study of 35 overweight/obese human subjects was conducted in Delaware in the United States by the marketer GOLO to determine the efficacy of a weight loss program "GOLO for Life". The study was conducted in the U.S. in 2010-2011 and recruited 49 subjects. Study participants were recruited through local newspaper ads and local postings. The study was comprised of weekly study visits with key data collected at baseline, 30 days, 90 days, and 26 weeks (Study 1), with an option for subjects to continue with the study for an additional 26 weeks (Study 1a). At study completion after 26 weeks, 23 subjects opted to continue on the program as a maintenance study for an additional 26 weeks. Each subject's baseline values were recorded and served as the basis by which the program's efficacy was measured.

TABLE 19

OVERVIEW OF STUDIES ON DIET PROGRAM.

| Study# | Location | N* | Weeks |
|---|---|---|---|
| 1 | United States | 35 | 26 |
| 1a | United States | 23 | 52 |

*N is the number of subjects completing the study. Study #1a is the continuation of study #1 after an additional 26-week follow-up.

The Diet Program

The diet program included behavior modification guidance in the form of booklets that included a self-assessment, an eating plan based on food groups, portion control and caloric restriction, and a dietary supplement as three capsules, three times per day. The supplement contained a blend of plant-derived ingredients and minerals consisting of banana leaf, barberry bark extract, apple fruit extract, *salacia* bark extract, *gardenia* fruit extract, *rhodiola* root, inositol, chromium, zinc and magnesium. The diet program used in this study may be best categorized as self-directed, with counseling and support available online, by email communications, or through a toll-free phone number. Subjects were provided with written handouts for the meal plan that included guidance on serving recommendations from the major food groups, with portion control and a self-assessment behavioral handout. Subjects were also provided with food and exercise logs. Subjects were directed to attempt 15 minutes of exercise per day or 105 minutes per week and to preferably exercise using high intensity workouts (HIT) such as walking with 30 second bursts and 30 second rest periods. Optional exercise classes were made available to the subjects twice per week.

Study Criteria

Adults older than 20 years old, with a body mass index>25 $kg/m^2$ were included in the study. Subjects were required to be healthy overweight or obese. Excluded were type 2 diabetics, pregnant or lactating subjects, determined by questionnaire, and individuals with known allergies to the dietary supplement or any of its ingredients. Subjects were instructed to continue to take all medications that they were taking at the time that the study began. Any subsequent changes in medication were made under supervision of the subjects' personal physician. Subjects were not compensated to join the trial or for participating in the trial.

Subjects were requested to visit the study center weekly with a minimum monthly visit to remain in the study. At each visit, body weight, body mass index (BMI), visceral fat, body fat, muscle loss and metabolic age as measured by a Tanita Body Composition Analyzer SC-331S were measured.

Body circumference measurements were taken at the waist, shoulders, chest, bicep, hips and thighs, and blood pressure (mmHg) and heart rate were also measured. Subjects provided completed food and exercise logs at the visit and their feedback on the Program. Subjects self-reported changes in dress and pants sizes. Front and side pictures of all subjects were taken at baseline and various intervals and at end points to verify results. Medication history and reduction or elimination of medications was also recorded.

At baseline, 3 months, and 6 months, blood work was taken and fasting blood glucose (mg/dL), HbA1c (% DCCT)

and blood lipids (triglycerides, total cholesterol, LDL, HDL) were measured using LabCorp or equivalent clinical chemistry providers.

Compliance

Compliance was measured at each weekly visit and at least monthly through exercise logs and food logs kept by subjects, and a count of supplement capsules remaining during each study visit. A minimum average compliance of 50% was required for inclusion in the data analysis. Compliance was based on level of adherence to diet, supplementation and exercise recommendations.

Ethical Requirements

Informed consent was obtained for all subjects. Study subjects were not compensated for participation. No institutional review board was used.

Data Analysis

Blake Ebersole (NaturPro Scientific LLC, Carmel, Indiana) reviewed all data provided by GOLO, LLC, evaluated the apparent integrity and completeness of the data, conducted statistical analysis, and wrote the report. All data from subjects completing the study were analyzed based on changes in endpoints from baseline using means, standard deviation and single-factor ANOVA using Microsoft Excel.

Results

Out of 49 subjects entering the study, 35 completed the full 26 week study. Of the 14 subjects who left the study, none were due to adverse events (Table 21). Data from dropouts were not included in the analysis of group results if they did not reach the 26 week mark and complete blood work. All drop out subjects lost weight, with data and reason for dropping out stated in Table 21 below.

Figure 2:
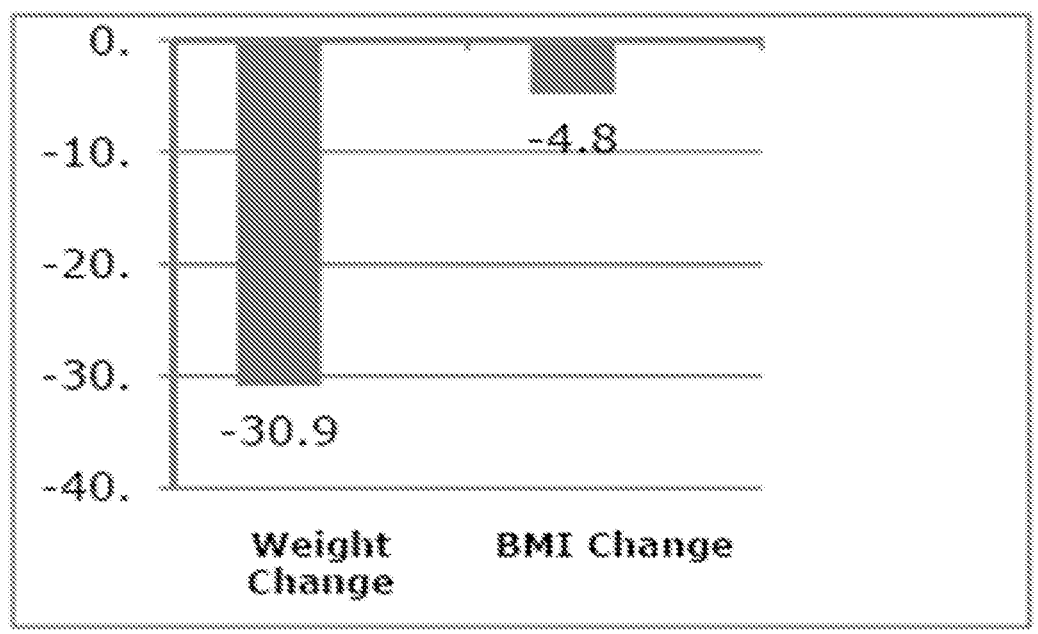
FIG. 2 illustrates change in average body weight (lb) and body mass index (BMI) after 26 weeks
Figure 3:
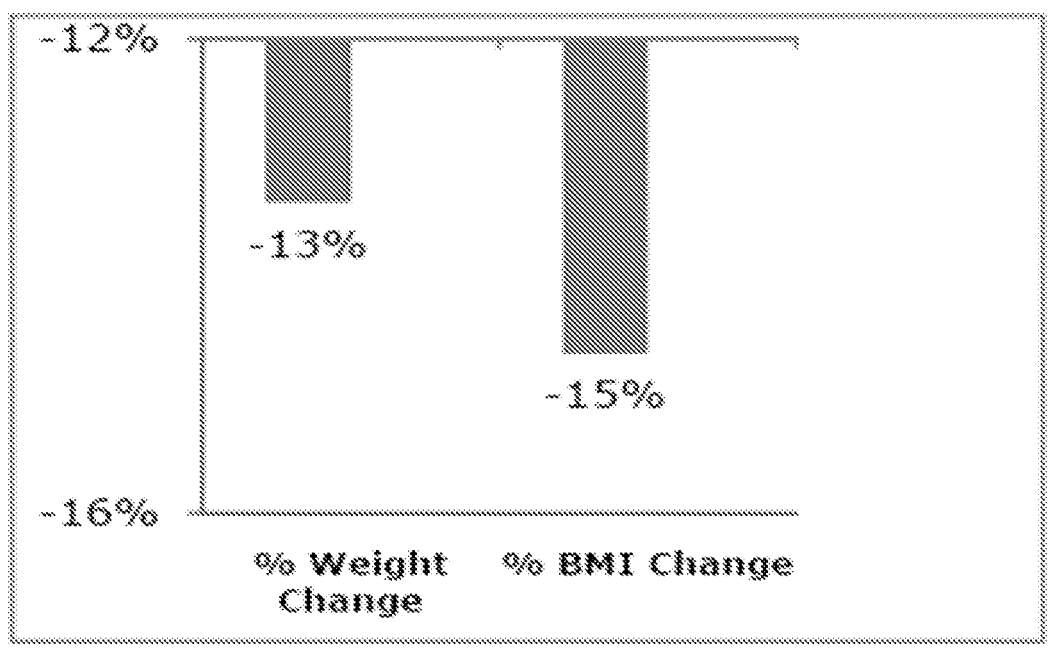
FIG. 3 illustrates change in average body weight and BMI after 26 weeks as a percentage of baseline values.
Figure 4:
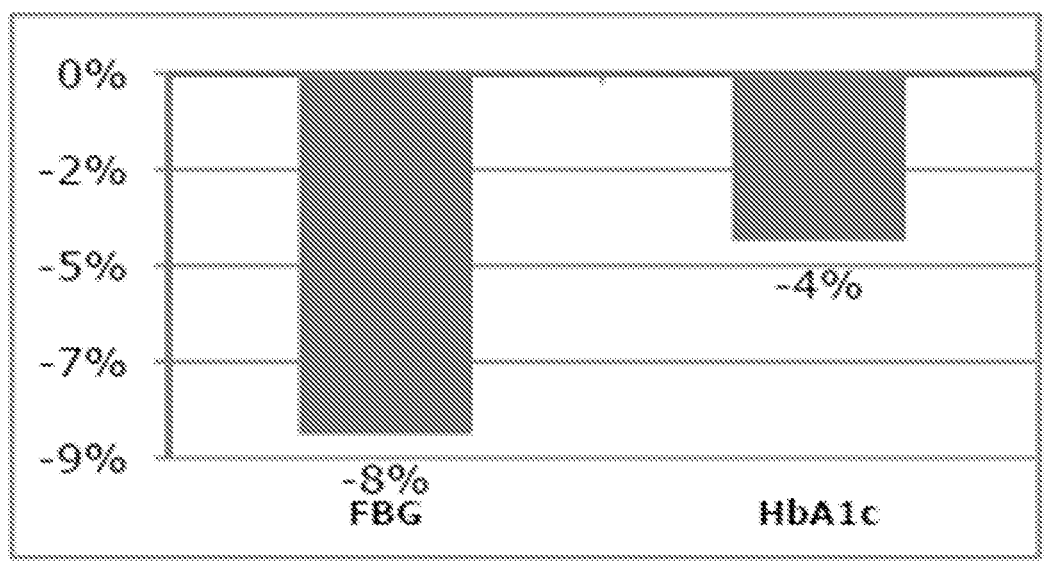
FIG. 4 illustrates change in average fasting blood glucose (FBG) and hemoglobin Ale from baseline to 26 weeks (n=35).

After 7 days, body weight in 34 subjects was reduced by an average of 3.4 lbs., and after 30 days, an average of 7.7 lbs. weight loss was observed (FIG. 1). One subject did not report data at 7 days and 30 days. After 90 days, average body weight was reduced by 20 pounds, and waist circumference was reduced by an average of four inches. After 26 weeks, the average weight loss was 30.9 pounds, which was significant from baseline ($p<0.005$) (FIG. 2). The average decrease in BMI at 26 weeks was 4.8 units (FIG. 3).

Average waist circumference, pants and dress size, fat percentage, total cholesterol, and triglycerides all decreased significantly from baseline after 26 weeks (Table 20). Muscle loss did not significantly decrease, suggesting the diet program reduced body fat without significant loss of muscle mass. For the subjects who remained in the study for an additional 26 weeks, all measures continued to be a significant reduction from baseline, except for total cholesterol.

TABLE 20

SUMMARY OF DATA IN THE U.S. DIET STUDY, BASED ON AVERAGE VALUES. VALUES IN RED WERE NOT SIGNIFICANT ($P > 0.05$).

|  | Baseline | 90 Day | 26 Weeks (n = 35) | 1 Year (n = 23) |
| --- | --- | --- | --- | --- |
| Weight (lbs) | 210.8 | 191.4<br>−19.3 ± 8.86<br>(p = 0.069) | 178.8<br>−30.9 ± 11.1<br>(p = 0.0024) | 167.8<br>−36.6 ± 14.7<br>(p = 0.000049) |
| Waist Circumference (in) | 42.1 | 39.0<br>−3.09 ± 1.70<br>(p = 0.02) | 35.7<br>−5.48 ± 1.75<br>(p = 0.000031) | 34.5<br>−6.94 ± 2.52<br>(p = 0.0000016) |
| BMI | 32.9 |  | 28.1<br>−4.8 ± 1.8<br>(p = 0.00084) | 25.9<br>−6.1 ± 3.0<br>(p = 0.0000025) |
| Dress Size | 16.2 |  | 9.33<br>−7 ± 2<br>(p = 0.000024) | 7.3<br>−8 ± 2<br>(p = 0.0000049) |
| Pants Size (waist inches) | 40.7 |  | 35.5<br>−5.27 ± 1.01<br>(p = 0.00025) | 33.6<br>−7.6 ± 2.6<br>(p = 0.00078) |
| Muscle (lbs) | 129.7 |  | 122.7<br>−7.1 ± 9.1<br>(p = 0.24) | 127.3<br>−2.3 ± 7.0<br>(p = 0.79) |
| % Muscle | 62.30% |  | 69.20%<br>6.9% ± 4.3%<br>(p = 0.00067) | 75.90%<br>12.5% ± 4.6%<br>(p = 0.0000017) |
| Fat (lbs) | 90.0 |  | 56.2<br>−23.8 ± 11.7<br>(p = 0.00074) | 40.4<br>−34.3 ± 12.6<br>(p = 0.000000017) |
| % Fat | 37.60% |  | 30.80%<br>−6.9% ± 4.3%<br>(p = 0.00068) | 24.10%<br>−12.5% ± 4.6%<br>(p = 0.0000017) |
| Cholesterol | 184.5 |  | 166.9<br>−17.6 ± 33.9<br>(p = 0.041) | 174.7<br>−7 ± 38<br>(p = 0.50) |
| LDL | 105.5 |  | 91.5<br>−13.9 ± 29.1<br>(p = 0.69) | 94.4<br>−8 ± 38<br>(p = 0.38) |
| HDL | 57.4 |  | 60.5<br>3.11 ± 9.93<br>(p = 0.41) | 64.8<br>9 ± 16<br>(p = 0.064) |

TABLE 20-continued

SUMMARY OF DATA IN THE U.S. DIET STUDY, BASED ON AVERAGE
VALUES. VALUES IN RED WERE NOT SIGNIFICANT (P > 0.05).

|  | Baseline | 90 Day | 26 Weeks (n = 35) | 1 Year (n = 23) |
|---|---|---|---|---|
| Triglyceride | 108.3 |  | 74.4 | 76.9 |
|  |  |  | −33.9 ± 48.1 | −37 ± 55 |
|  |  |  | (p = 0.0037) | (p = 0.0067) |
| CHL/HDL ratio | 3.51 |  | 2.88 | 2.88 |
|  |  |  | −0.63 ± 0.90 | −0.64 ± 1.23 |
|  |  |  | (p = 0.020) | (p = 0.07) |
| HDL/LDL ratio | 2.05 |  | 1.61 | 1.61 |
|  |  |  | −0.44 ± .070 | −0.42 ± 0.98 |
|  |  |  | (p = 0.035) | (p = 0.23) |

Figure 5:
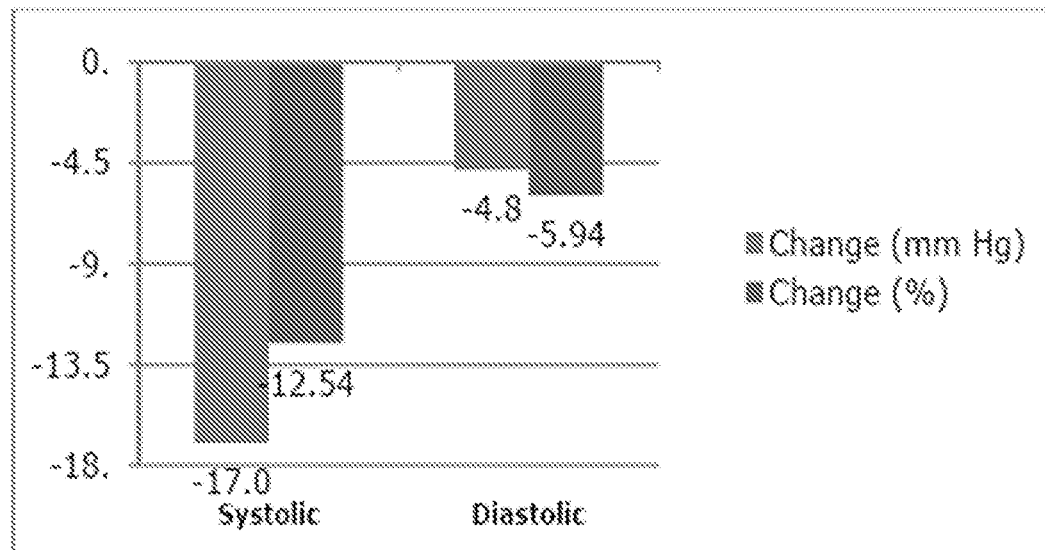
FIG. 5 illustrates change in average blood pressure from baseline to 26 weeks (n=35).

According to the NIDDK, fasting blood glucose and hemoglobin A1c (HbA1c) are primary indicators of blood sugar health and insulin resistance. At 26 weeks fasting blood glucose was reduced by an average of 8.5% (p<0.01) and HbA1c was reduced by an average of 3.9% (5.79 to 5.56, p=0.011) (FIG. 5). In a subset of 24 healthy pre-diabetic subjects with baseline HbA1c levels between 5.7 and 7.1, an average 6.9% decrease was found at 90 days (p<0.0001). A 4% average reduction was observed after 26 weeks, which was significant (p=0.002). At 52 weeks, an average 7.3% decrease was found in these subjects (p<0.001).

Figure 6:
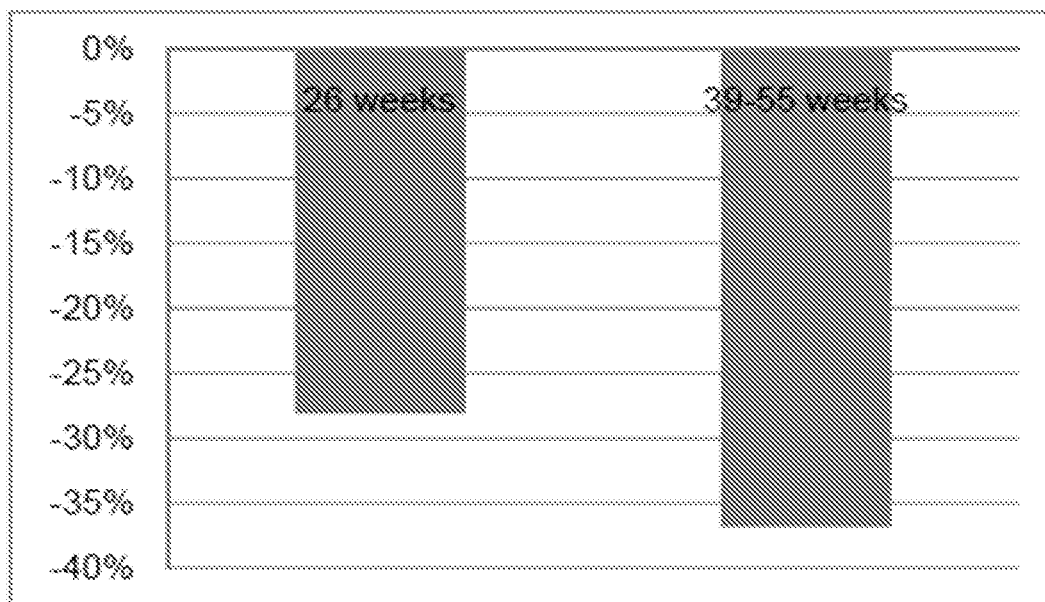
FIG. 6 illustrates change in average visceral fat (%) over 26 weeks (p=0.005) and over 39-55 weeks (p<0.00001) (n=35)).

In all subjects, average systolic and diastolic blood pressure was reduced by 12.5% (p<0.001) and 6.0% (p<0.05), respectively after 26 weeks (FIG. 6).

Visceral fat was significantly reduced over 26 weeks by an average of 28% (from 10.00% to 7.19%, p=0.005, FIG. 7) and by an average of 37% in subjects who continued for 39-55 weeks (from 10.00% to 6.32%, p<0.0001). Of the 35 subjects, 11 had a visceral fat percentage greater than 13% at the start (average 15.82%). At 26 weeks, the average visceral fat percentage for these 11 subjects was 11.45%.

Metabolic age, calculated from body composition analysis, also decreased from an average of 56.3 to 43.2 years of age (p<0.0001) at 26 weeks. Although metabolic age is an estimated value, it can be used as supportive data with respect to the number of other improvements observed in this study on primary biomarkers such as body weight.

Fourteen (14) of the USA study participants had been prescribed a total of 35 medications at the start of the study. After 26 weeks, more than half (18) prescription medications were eliminated, and 6 were prescribed at a lower dosage, all under the supervision of the subjects' personal physician. 14 subjects left the study before 26 weeks due to various factors (Table 21). No dropouts were due to adverse events. All dropouts showed a reduction in weight.

TABLE 21

BODY WEIGHT CHANGES FROM SUBJECTS
WHO DISCONTINUED THE 26-WEEK STUDY.

| Baseline (lb) | End (lb) | Difference (lb) | Weeks in Study | Reasons |
|---|---|---|---|---|
| 227 | 212.6 | −14.4 | 16 | Family issues |
| 205 | 191.6 | −13.4 | 12 | Unknown |
| 173.4 | 165.6 | −7.8 | 10 | Moved away |
| 225.8 | 221.6 | −4.2 | 9 | Husband made her stop |
| 140.4 | 135.6 | −4.8 | 7 | Work |
| 240.4 | 229.6 | −10.8 | 5 | Drug problem |
| 210.4 | 199.8 | −10.6 | 5 | Mother sick |
| 274.6 | 268.2 | −6.4 | 8 | Health issues |

TABLE 21-continued

BODY WEIGHT CHANGES FROM SUBJECTS
WHO DISCONTINUED THE 26-WEEK STUDY.

| Baseline (lb) | End (lb) | Difference (lb) | Weeks in Study | Reasons |
|---|---|---|---|---|
| 168.8 | 155.6 | −13.2 | 14 | Travelling time |
| 151.2 | 123.2 | −28 | 14 | Time issues |
| 184.6 | 177.2 | −7.4 | 7 | Scheduling conflicts |
| 165.4 | 145.2 | −20.2 | 20 | Time issues |
| 151.4 | 139.6 | −11.8 | 15 | Pregnancy |
| 232.4 | 218 | −14.4 | 13 | Changed jobs-too far |

Discussion

The diet program used in this study combines diet, exercise and nutritional supplementation together into a self-directed program. A number of studies have been performed using similar diet programs. A recent meta-analysis was performed that categorized randomized controlled human trials on diet programs into three categories: 1) "market leaders" such as Nutri-System® and Weight Watchers®, 2) very-low-calorie meal replacements, and 3) self-directed programs such as Atkins® and SlimFast®. Most of the diet plans studied combine face-to-face and group counseling, medical supervision, packaged foods or diet plans, and exercise recommendations.

The range of weight loss in 6-month studies on market leaders was between 3.6 and 8.1% of total body weight. Meanwhile, weight loss for very-low-calorie meal replacement programs ranged between 1.9 and 22% for study durations between 3 and 9 months, with most studies reporting an average reduction lower than 8%. For self-directed programs, studies ranging from 3-12 months demonstrated a range of average weight loss between 0 and 8.7%, with the predominant number of studies averaging less than 5% weight loss. The diet program used in this study may be best categorized as self-directed, with counseling and support available online, by email communications, or through a toll-free phone number. In this study, an average weight loss of 13% was observed in 26 weeks, which compares favorably to previous studies on self-directed programs. In addition to improvements in body weight and BMI, a number of blood markers associated with poor diet, cardiometabolic syndromes, and insulin resistance, including fasting blood sugar and HbA1c, were also improved compared to baseline values.

Glycated hemoglobin A1c (HbA1c) is a marker long used by physicians to determine a patient's average blood glucose levels over the previous 8-12 weeks. For this reason, HbA1c is generally considered a more reliable marker than fasting blood glucose to reflect average levels of blood glucose. Insulin resistance occurs when cells in the body are less responsive to insulin, which can lead to increases in blood sugar reflected in HbA1c and FBG levels. Thus, a reduction in HbA1c levels, along with improvements in body weight, together may indicate an improvement in insulin resistance. For example, changes in insulin resistance and HbA1c can be caused by exercise-mediated changes in body composition in older adults with type-2 diabetes. Other diet programs have also measured improvements in HbA1c and body weight. A 2016 study on Weight Watchers® showed a significant 6-month weight loss of 5.5%, and a significant decrease in HbA1c in pre-diabetic subjects following the program. A health coaching program in diabetics with a low socioeconomic status was also shown to reduce body weight, waist circumference and HbA1c.

The diet program used in the current study appeared to improve body weight favorably, consistent with previous studies on other similar diet programs. The diet program used in this study was affordable and did not require office visits, or food to be purchased, aside from an included dietary supplement requiring the consumption of three capsules per day. These factors could help to contribute to long-term compliance for a broader spectrum of people, as well as for those who have more weight to lose and need a long-term weight loss plan.

As with any study, dropouts and side effects can be a concern for weight loss plans. However dropouts from the studies all had reduced body weight at the time of withdrawal, and no withdrawals were due to treatment or study-related effects. Based on this early data, the diet program in this study may be an effective program that can be self-directed and also easily monitored by health coaches or physicians.

Although subjects were used as their own controls in this study, data from control groups in studies of other diet programs allow for some meaningful comparisons to be made. The amount and percentage of weight loss observed in this study was consistent with data reported by similar programs such as Weight Watchers and Nutrisystem. Despite the lack of a separate control group, an abundance of control data has been published. Further, the high degree of clinical relevance and supporting evidence on the individual elements of the intervention in this study adds a considerable degree of strength to the results observed. Larger studies are planned on the program to determine whether the effects observed can be repeated in other populations, and in larger sample sizes over longer durations.

Overall, subjects in this study showed significant reductions in body weight and BMI, and also experienced improvements in several markers of metabolic function. The data is consistent with previous results from the program, and with published data supporting the elements of the program. Thus, the effects observed in this study on a combination of dietary and behavioral interventions support the effectiveness of the GOLO for Life program for weight loss and several related clinical endpoints.

TABLE 22

INDIVIDUAL WEIGHT LOSS AFTER 26 WEEKS.

| Subject # | Baseline (lb) | 26 weeks (lb) | Difference (lb) | Difference (%) |
|---|---|---|---|---|
| 1 | 205.8 | 174.6 | −31.2 | −15% |
| 2 | 220.8 | 189.2 | −31.6 | −14% |
| 3 | 238.0 | 203.6 | −34.4 | −14% |
| 4 | 205.0 | 189.0 | −16.0 | −8% |
| 5 | 155.6 | 143.0 | −12.6 | −8% |
| 6 | 177.8 | 152.6 | −25.2 | −14% |
| 7 | 238.0 | 185.2 | −52.8 | −22% |
| 8 | 192.6 | 156.0 | −36.6 | −19% |
| 9 | 246.0 | 206.0 | −40.0 | −16% |
| 10 | 220.2 | 184.4 | −35.8 | −16% |
| 11 | 156.8 | 135.8 | −21.0 | −13% |
| 12 | 197.0 | 153.4 | −43.6 | −22% |
| 13 | 182.6 | 152.6 | −30.0 | −16% |
| 14 | 213.8 | 183.0 | −30.8 | −14% |
| 15 | 233.0 | 190.6 | −42.4 | −18% |
| 16 | 182.6 | 163.6 | −19.0 | −10% |
| 17 | 375.4 | 332.4 | −43.0 | −11% |
| 18 | 188.0 | 162.8 | −25.2 | −13% |
| 19 | 201.4 | 161.8 | −39.6 | −20% |
| 20 | 250.2 | 221.6 | −28.6 | −11% |
| 21 | 173.2 | 144.0 | −29.2 | −17% |
| 22 | 172.0 | 157.2 | −14.8 | −9% |
| 23 | 183.2 | 152.8 | −30.4 | −17% |
| 24 | 206.4 | 160.4 | −46.0 | −22% |
| 25 | 173.4 | 139.6 | −33.8 | −19% |
| 26 | 240.2 | 188.6 | −51.6 | −21% |
| 27 | 273.8 | 241.2 | −32.6 | −12% |
| 28 | 265.0 | 226.0 | −39.0 | −15% |
| 29 | 237.4 | 198.2 | −39.2 | −17% |
| 30 | 248.8 | 239.6 | −9.2 | −4% |
| 31 | 162.2 | 141.0 | −21.2 | −13% |
| 32 | 183.4 | 160.8 | −22.6 | −12% |
| 33 | 189.2 | 151.0 | −38.2 | −20% |
| 34 | 172.4 | 161.0 | −11.4 | −7% |
| 35 | 180.0 | 157.0 | −23.0 | −13% |
| Average | 209.7 | 178.8 | −30.9 | −15% |

TABLE 23

SUMMARY OF RESULTS AFTER 26 WEEKS.
26 Week USA Summary

| Participants | # | 35 |
|---|---|---|
| Trial Length | weeks | 26 |
| Average Weight | lb | −30.9 |
| Average Weight Change Per Week | lb | −1.2 |
| % Body Weight | % | −13.4 |
| Muscle Mass | lb | −7.1 |
| Fat | lb | −23.8 |
| BMI | % | −14.6 |
| Visceral Fat | % | −27.9 |
| Total Inches | inches | −23.3 |
| Waist Size | inches | −6.0 |
| Dress Size | Sizes | −3.4 |
| Pants Size | Sizes | −5.3 |
| Food Compliance | % | 73.9 |
| Exercise Compliance | % | 73.2 |
| Blood Pressure Systolic | % | −12.5 |
| Blood Pressure Diastolic | % | −5.9 |
| Total Cholesterol | % | −9.6 |
| LDL | % | −13.2% |
| HDL | % | 5.4% |
| Triglycerides | % | −31.3% |
| Glucose | % | −8.5% |
| A1C | % | −3.9% |
| Cholesterol/HDL Ratio | % | −14.2% |
| LDL/HDL Ratio | % | −17.7% |
| Metabolic Syndrome Risk Factors | Baseline | 114 |
| Metabolic Syndrome Risk Factors | 26 wks. | 50 |
| Metabolic Syndrome | Baseline | 24 |
| Metabolic Syndrome | 26 wks. | 5 |
| Pre Diabetic | Baseline | 23 |
| Pre Diabetic | 26 wks. | 12 |

Example 4

Further studies have been planned to further evidence the surprising and unexpected results shown in previous studies. Such studies may be a multi-arm study, such as two arm, three arm or four arm study for the weight loss composition, the weight management plan, and/or the bulk food product of embodiments herein. An exemplary study may include a comparison of the weight management composition of embodiments herein to a placebo, the weight management composition of embodiments herein and the weight management plan of embodiments herein to a placebo, and/or the weight management composition of embodiments herein and the weight management plan of embodiments herein to a control diet. The planned studies are expected to fully support the superior results seen in past studies.

Although the present invention has been described in considerable detail with reference to certain preferred embodiments thereof, other versions are possible. Therefore the spirit and scope of the appended claims should not be limited to the description and the preferred versions contained within this specification.

The invention claimed is:

1. A weight loss composition, a daily dosage of the composition comprising: banaba leaf extract in an amount of about 20 mg to about 100 mg; apple fruit extract in an amount of about 30 mg to about 100 mg; *Rhodiola* root extract in an amount of about 140 mg to about 400 mg; chromium chelate; magnesium chelate; and zinc chelate.

2. The weight loss composition of claim 1, wherein the amount of chromium in the daily dosage ranges from about 100 mcg to about 300 mcg.

3. The weight loss composition of claim 1, wherein the amount of magnesium in the daily dosage ranges from about 5 mg to about 100 mg.

4. The weight loss composition of claim 1, wherein the amount of zinc in the daily dosage ranges from about 5 mg to about 40 mg.

5. The weight loss composition of claim 1, further comprising *gardenia* fruit extract, *Salacia* extract, inositol, berberine, or combinations thereof.

6. The weight loss composition of claim 5, wherein the amount of *gardenia* fruit extract in the daily dosage ranges from about 25 mg to about 200 mg.

7. The weight loss composition of claim 5, wherein the amount of *Salacia* extract in the daily dosage ranges from about 10 mg to about 400 mg.

8. The weight loss composition of claim 5, wherein the amount of inositol in the daily dosage ranges from about 100 mg to about 300 mg.

9. The weight loss composition of claim 5, wherein the amount of berberine in the daily dosage ranges from about 50 mg to about 200 mg.

10. A weight loss composition, a daily dosage of the composition comprising: banaba leaf extra in an amount of about 56 mg; apple fruit extract in an amount of about 45 mg; *Rhodiola* root extract in an amount of about 340 mg; chromium chelate, with an amount of chromium of about 210 mcg; magnesium chelate, with an amount of magnesium of about 45 mg; and zinc chelate, with an amount of zinc of about 30 mg.

11. The weight loss composition of claim 10, further comprising: berberine hydrochloride in an amount of about 105 mg; inositol in an amount of about 210 mg; *Salacia* extract in an amount of about 45 mg; and *gardenia* fruit extract in an amount of about 90 mg.

12. A kit, comprising: the weight loss composition of claim 1; and instructions for a weight management plan designed to stabilize and optimize insulin levels.

13. A weight loss composition, the daily dosage of the composition comprising: banaba leaf extract in an amount of about 56 mg; apple fruit extract in an amount of about 45 mg; *Rhodiola* root extract in an amount of about 340 mg; chromium chelate, with an amount of chromium of about 210 mcg; magnesium chelate, with an amount of magnesium of about 45 mg; and zinc chelate, with an amount of zinc of about 30 mg. berberine hydrochloride in an amount of about 105 mg; inositol in an amount of about 210 mg; *Salacia* extract in an amount of about 45 mg; and *gardenia* fruit extract in an amount of about 90 mg.

* * * * *